(12) United States Patent
Hamada et al.

(10) Patent No.: US 8,883,078 B2
(45) Date of Patent: Nov. 11, 2014

(54) SAMPLE TESTING SYSTEM AND TRANSPORTING APPARATUS

(75) Inventors: Yuichi Hamada, Kobe (JP); Daigo Fukuma, Kobe (JP)

(73) Assignee: Sysmex Corporation, Kobe (JP)

( * ) Notice: Subject to any disclaimer, the term of this patent is extended or adjusted under 35 U.S.C. 154(b) by 936 days.

(21) Appl. No.: 12/645,930

(22) Filed: Dec. 23, 2009

(65) Prior Publication Data
US 2010/0166605 A1    Jul. 1, 2010

(30) Foreign Application Priority Data
Dec. 26, 2008    (JP) .................. 2008-334774

(51) Int. Cl.
| | | |
|---|---|---|
| *G01N 35/04* | (2006.01) | |
| *G01N 35/10* | (2006.01) | |
| *G01N 35/02* | (2006.01) | |
| *G01N 35/00* | (2006.01) | |

(52) U.S. Cl.
CPC ............ *G01N 35/02* (2013.01); *G01N 35/0092* (2013.01); *G01N 2035/0472* (2013.01); *G01N 2035/0465* (2013.01); *G01N 35/026* (2013.01); *G01N 2035/0462* (2013.01); *G01N 35/021* (2013.01)
USPC ................ 422/65; 422/63; 436/47; 436/49

(58) Field of Classification Search
USPC ............ 422/63, 65, 297, 300; 436/45, 46, 48; 414/331.03
See application file for complete search history.

(56) References Cited

U.S. PATENT DOCUMENTS

| | | | |
|---|---|---|---|
| 6,019,945 A * | 2/2000 | Ohishi et al. ................ | 422/65 |
| 6,117,392 A | 9/2000 | Hanawa et al. | |
| 2005/0036913 A1 | 2/2005 | Yamakawa et al. | |
| 2005/0196320 A1* | 9/2005 | Veiner et al. ................ | 422/63 |
| 2006/0216199 A1* | 9/2006 | Koike ........................... | 422/65 |

FOREIGN PATENT DOCUMENTS

| | | | |
|---|---|---|---|
| JP | 09-43249 | * | 2/1997 |
| JP | 2008-032652 | * | 2/2008 |

* cited by examiner

*Primary Examiner* — P. Kathryn Wright
(74) *Attorney, Agent, or Firm* — Brinks Gilson & Lione

(57) ABSTRACT

A sample testing system comprising: a test unit for loading and testing a sample contained in the sample container accommodated in the rack; a rack storage for storing the rack accommodating the sample container from which the sample has been loaded into the test unit; and a transporting part, configured to transport the rack in a first direction and in a second direction that is a reverse direction of the first direction, for transporting the rack in the first direction to the rack storage and transporting the rack stored in the rack storage in the second direction to a sample loading position at which the sample is loaded from the rack into the test unit, is disclosed. A transporting apparatus is also disclosed.

18 Claims, 21 Drawing Sheets

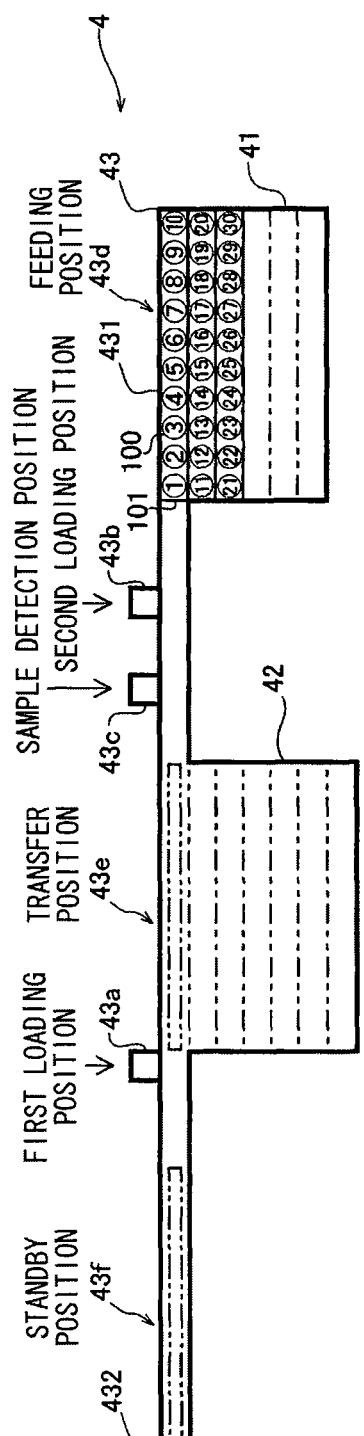
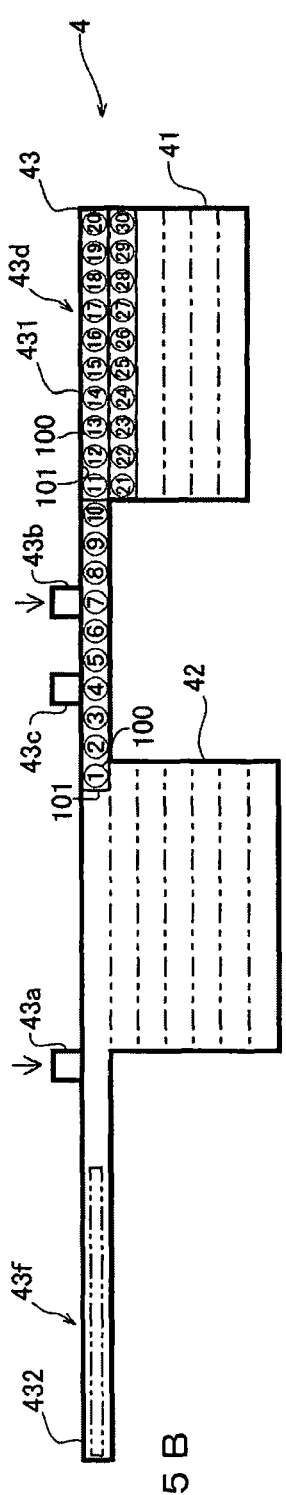
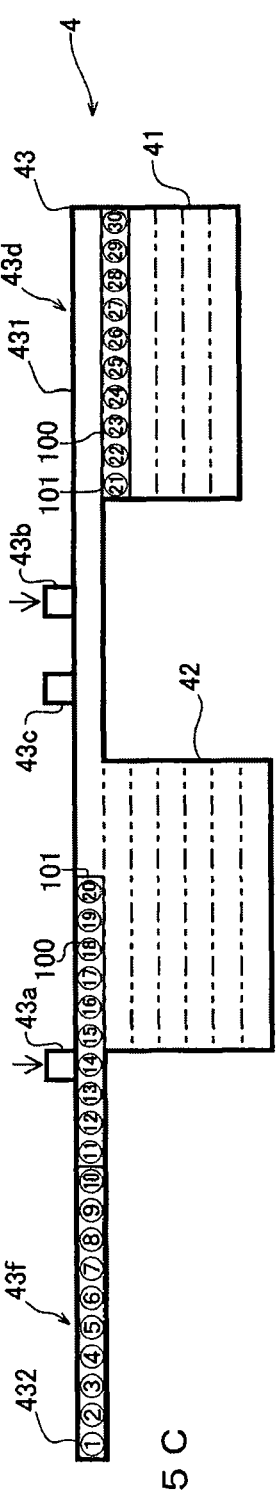

SAMPLE TESTING SYSTEM AND TRANSPORTING APPARATUS

RELATED APPLICATIONS

This application claims priority under 35 U.S.C. §119 to Japanese Patent Application No. JP2008-334774 filed on Dec. 26, 2008, the entire content of which is hereby incorporated by reference.

BACKGROUND OF THE INVENTION

1. Field of the Invention

The present invention relates to a sample testing system, and particularly to a sample testing system that includes a transporting part for transporting a rack that accommodates sample containers. Also, the present invention relates to a transporting apparatus.

2. Description of the Related Art

Conventionally, there are known sample testing apparatuses that include a transporting apparatus for transporting sample containers each containing a sample. As for such a sample testing apparatus, there is a case where after a sample is loaded into, and tested by, the sample testing apparatus, retesting of the sample becomes necessary. Whether or not retesting of the sample is necessary is determined after the sample is loaded into the sample testing apparatus and a result of testing the sample by the sample testing apparatus is obtained. Accordingly, the sample that has been loaded stands by on a transporting path until it is determined whether or not retesting of the sample is necessary. This hinders the following samples from moving toward a collecting unit, resulting in stagnant sample transportation. Therefore, sample processing cannot be performed efficiently.

U.S. Pat. No. 6,117,392 discloses, as a sample testing apparatus that enables efficient sample processing, an automatic analyzing apparatus that includes: an analyzing unit for analyzing samples; and a transporting apparatus for transporting, to the analyzing unit, racks each holding multiple sample containers containing samples. The transporting apparatus of the automatic analyzing apparatus includes: a transporting line for transporting each rack that holds multiple sample containers; a standby unit for taking in, from the transporting line in a direction perpendicular to the transporting line, a rack that holds samples having been measured by the analyzing unit, and for allowing the rack to stand by therein until it is determined whether or not retesting of the samples in the rack is necessary; and a returning line, provided separately from the transporting line, for sending a rack that holds samples to be retested, to the upstream side of the transporting line. Racks transported on the transporting line are each, after the analyzing unit has performed sample loading from each sample container thereof, taken in and held by the standby unit until it is determined whether or not retesting of the samples therein is necessary. Then, a rack that holds samples for which retesting has been determined to be necessary, is returned from the standby unit through the returning line to the upstream side of the transporting line (i.e., to a position at which the transporting starts). By having the above configuration, a rack that holds samples that are waiting for necessity/unnecessity determination for retesting can be kept standing by at the standby unit, during which the following rack that holds samples for which retesting has been determined to be unnecessary can be collected into a collecting unit. Thus, the transporting of the racks is not stagnated, and the processing can be performed efficiently.

However, in the automatic analyzing apparatus described in U.S. Pat. No. 6,117,392, the transporting line is capable of transporting racks only in a single direction. Therefore, although the transporting line can transport racks from the analyzing unit to the standby unit or to the collecting unit, the transporting line cannot transport a rack that holds samples that require retesting, from the standby unit to the analyzing unit. For this reason, it is necessary to provide, separately from the transporting line, the returning line for transporting the rack from the standby unit to the upstream side of the transporting line. This results in a problem that the analyzing apparatus becomes large sized.

SUMMARY OF THE INVENTION

The scope of the invention is defined solely by the appended claims, and is not affected to any degree by the statements within this summary.

A first aspect of the present invention is a sample testing system comprising: a test unit for loading and testing a sample contained in the sample container accommodated in the rack; a first rack storage for storing the rack accommodating the sample container from which the sample has been loaded into the test unit; and a transporting part, configured to transport the rack in a first direction and in a second direction that is a reverse direction of the first direction, for transporting the rack in the first direction to the first rack storage and transporting the rack stored in the first rack storage in the second direction to a sample loading position at which the sample is loaded from the rack into the test unit.

A second aspect of the present invention is a transporting apparatus for transporting a sample to a test unit that performs loading and testing of the sample contained in a sample container accommodated in a rack, the transporting apparatus comprising: a first rack storage for storing the rack accommodating the sample container from which the sample has been loaded into the test unit; and a transporting part, configured to transport the rack in a first direction and in a second direction that is a reverse direction of the first direction, for transporting the rack in the first direction to the first rack storage and transporting the rack stored in the first rack storage in the second direction to a sample loading position at which the sample is loaded from the rack into the test unit.

BRIEF DESCRIPTION OF THE DRAWINGS

FIGS. 5A to 5C are schematic diagrams illustrating positional relationships within the sample transporting apparatus of the blood analyzer according to the embodiment shown in FIG. 1;

DETAILED DESCRIPTION OF THE PREFERRED EMBODIMENTS

Hereinafter, an embodiment of a sample testing apparatus of the present invention will be described in detail with reference to the accompanying drawings.

Figure 1:
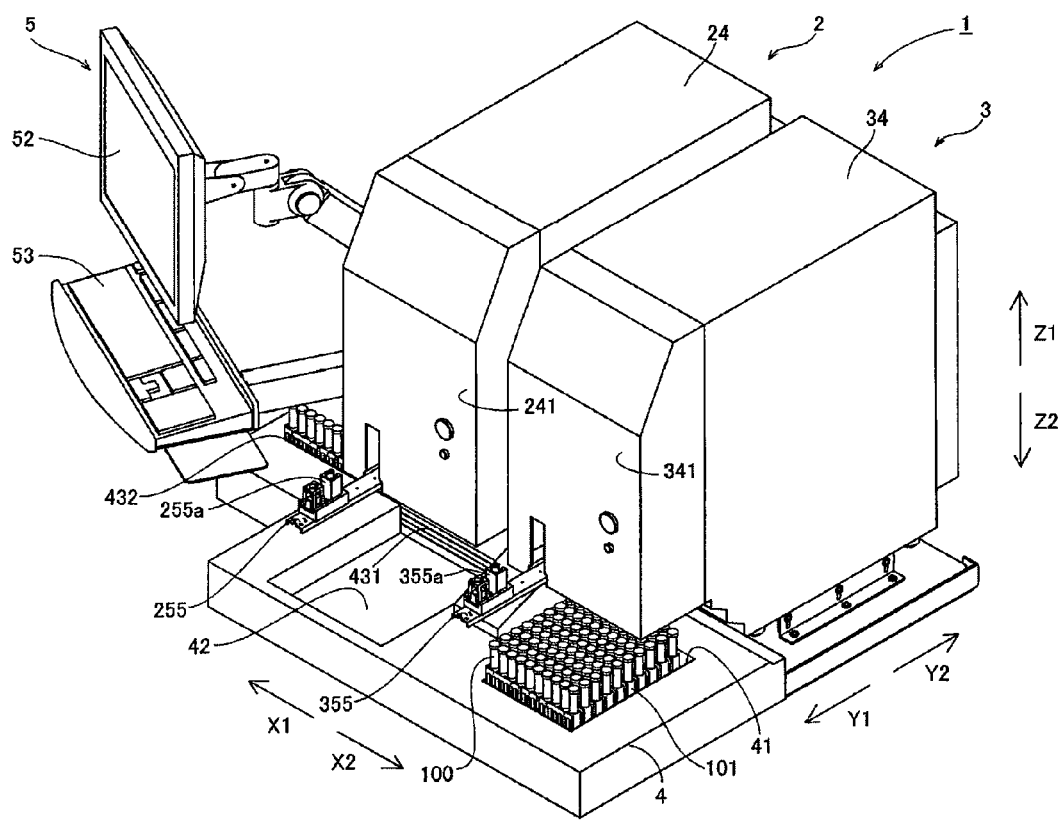
FIG. 1 is a perspective view showing an overall configuration of a blood analyzer according to an embodiment of the present invention.

FIG. 1 is a perspective view showing an overall structure of a blood analyzer according to the embodiment of the present invention. FIGS. 2 to 9 each illustrate, in detail, components of the blood analyzer according to the embodiment shown in FIG. 1. First, an overall structure of a blood analyzer 1 according to the embodiment of the present invention will be described with reference to FIGS. 1 to 9. Note that the present embodiment describes a case where the present invention is applied in the blood analyzer 1 that is an example of the sample testing apparatus.

As shown in FIG. 1, the blood analyzer 1 according to the present embodiment includes: two measurement units that are a first measurement unit 2 and a second measurement unit 3; a sample transporting apparatus (sampler) 4 disposed in front of the first measurement unit 2 and the second measurement unit 3 (i.e., disposed on an arrow Y1 direction side); and a control apparatus 5 structured as a PC (Personal Computer) that is electrically connected to the first measurement unit 2, the second measurement unit 3, and the sample transporting apparatus 4. Further, the blood analyzer 1 is connected to a host computer 6 (see FIG. 2) via the control apparatus 5.

Figure 2:
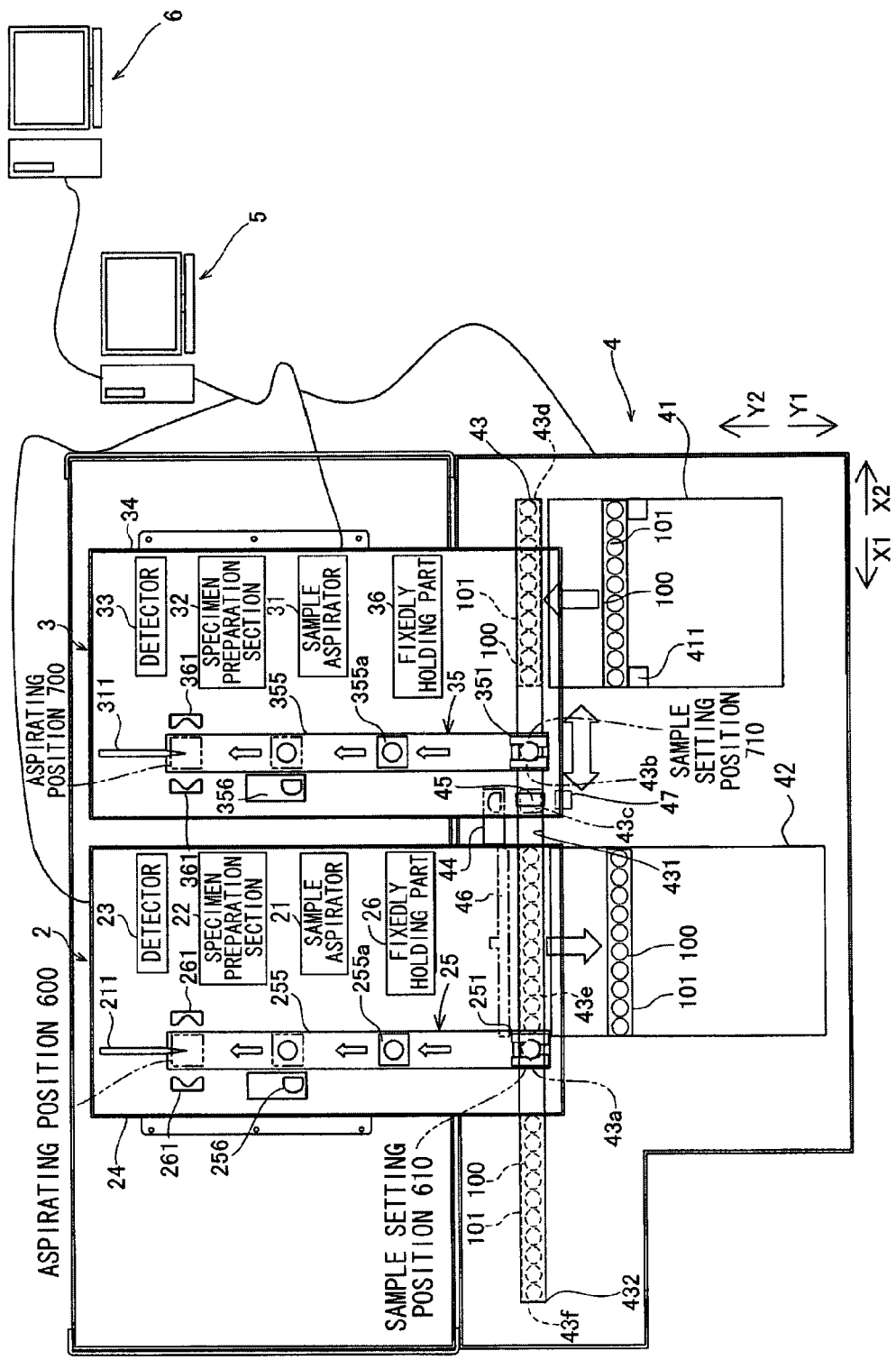
FIG. 2 is a schematic diagram showing measurement units and a sample transporting apparatus of the blood analyzer according to the embodiment shown in FIG. 1.
Figure 3:
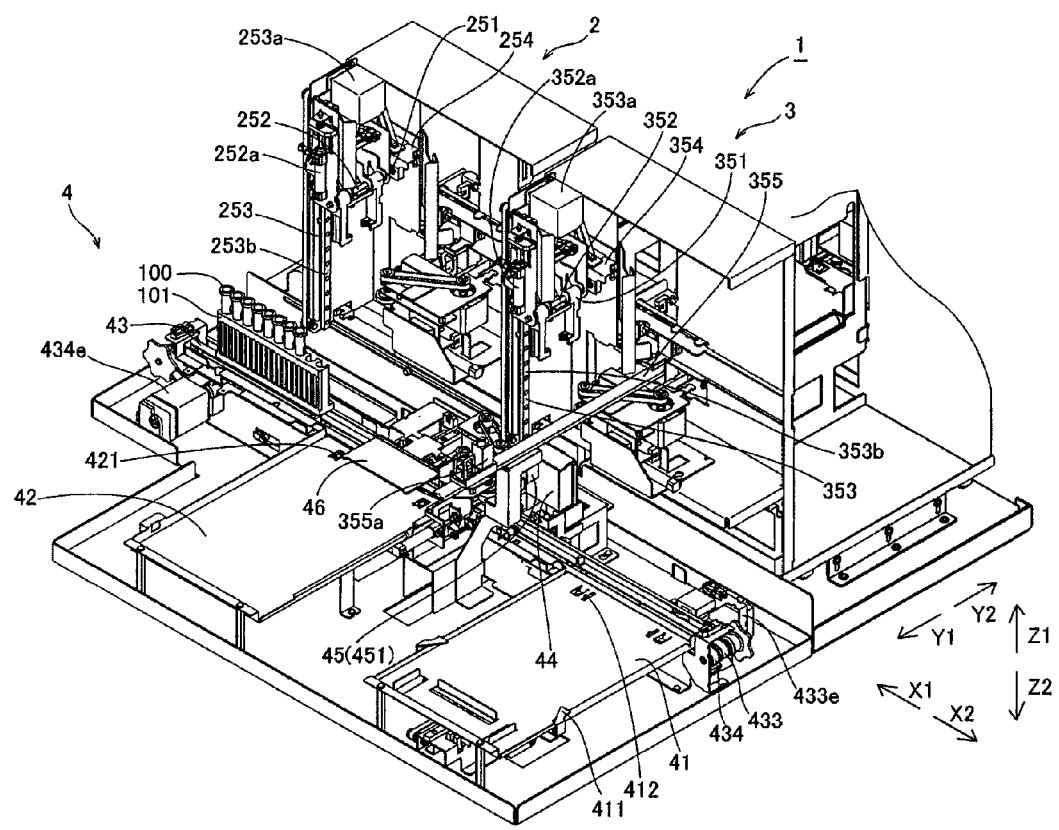
FIG. 3 is a perspective view showing the measurement units and the sample transporting apparatus of the blood analyzer according to the embodiment shown in FIG. 1.

Further, as shown in FIGS. 1 to 3, the first measurement unit 2 and the second measurement unit 3 are measurement units of practically the same type, which are arranged so as to be adjacent to each other. To be specific, in the present embodiment, the second measurement unit 3 uses the same measurement principle as that of the first measurement unit 2 to measure a sample for the same measurement item as that of the first measurement unit 2. As shown in FIG. 2, the first measurement unit 2 includes: a sample aspirator 21 for aspirating a blood sample from a sample container (test tube) 100; a specimen preparation section 22 for preparing a detection specimen from the blood aspirated by the sample aspirator 21; and a detector 23 for detecting blood cells from the detection specimen prepared by the specimen preparation section 22. Also, the second measurement unit 3 includes: a sample aspirator 31 for aspirating a blood sample from a sample container (test tube) 100; a specimen preparation section 32 for preparing a detection specimen from the blood aspirated by the sample aspirator 31; and a detector 33 for detecting blood cells from the detection specimen prepared by the specimen preparation section 32.

As shown in FIG. 2, the first measurement unit 2 further includes: a unit cover 24 for accommodating therein the sample aspirator 21, the specimen preparation section 22, and the like; a sample container transporter 25 for loading a sample container 100 into the inside of the unit cover 24 and for transporting the sample container 100 to an aspirating position 600 of the sample aspirator 21; and a fixedly holding part 26 for fixedly holding the sample container 100 in the aspirating position 600. Also, the second measurement unit 3 further includes: a unit cover 34 for accommodating therein the sample aspirator 31, the specimen preparation section 32, and the like; a sample container transporter 35 for loading a sample container 100 into the inside of the unit cover 34 and for transporting the sample container 100 to an aspirating position 700 of the sample aspirator 31; and a fixedly holding part 36 for fixedly holding the sample container 100 in the aspirating position 700.

As shown in FIG. 2, the sample aspirator 21 (31) includes a piercer 211 (311). The tip of the piercer 211 (311) is formed so as to be able to penetrate (pierce) through a below-described sealing cap 100a (see FIG. 4) of a sample container 100. Further, the piercer 211 (311) is configured to move in vertical directions (arrow Z1 and Z2 directions) through an operation of a piercer drive section that is not shown.

The detector 23 (33) is configured to perform RBC detection (detection of red blood cells) and PLT detection (detection of platelets) by the sheath flow DC detection method, and to perform HGB detection (detection of hemoglobin in blood) by the SLS-hemoglobin method. The detector 23 (33) is also configured to perform WBC detection (detection of white blood cells) by flow cytometry using semiconductor laser. Detection results obtained by the detector 23 (33) are transmitted to the control apparatus 5 as measurement data (measurement results) of a sample. Note that the measurement data is used as a basis for final analysis results (such as a red blood count, platelet count, amount of hemoglobin, white blood count, and the like) provided to a user.

As shown in FIG. 3, the sample container transporter 25 (35) has: a hand part 251 (351) capable of holding a sample container 100; an opening/closing part 252 (352) capable of opening/closing the hand part 251 (351); a vertically moving part 253 (353) for rectilinearly moving the hand part 251 (351) in vertical directions (the arrow Z1 and Z2 directions); and an agitator 254 (354) for moving the hand part 251 (351) in the vertical directions (the arrow Z1 and Z2 directions) in a swinging manner. Further, as shown in FIG. 2, the sample container transporter 25 (35) has: a sample container moving part 255 (355) for horizontally moving a sample container 100 in the arrow Y1 and Y2 directions; and a bar code reader 256 (356).

The hand part 251 (351) is disposed above a transporting part of the sample transporting apparatus 4 that transports a rack 101. The hand part 251 (351) is configured to, when a sample container 100 has been transported by the sample transporting apparatus 4 to a below-described first loading position 43a (second loading position 43b)(see FIG. 2), move downward (in the arrow Z2 direction) and then be caused by the opening/closing part 252 (352) to open and close to hold the sample container 100 that is accommodated in the rack 101.

Further, the hand part 251 (351) is configured to move the held sample container 100 upward (in the arrow Z1 direction) to remove the sample container 100 from the rack 101, and then be moved in a swinging manner by the agitator 254 (354) (e.g., 10 reciprocating swinging movements). In this manner, the hand part 251 (351) is capable of agitating the blood contained in the held sample container 100. The hand part 251 (351) is configured to move, after the agitation has ended, downward (in the arrow Z2 direction) and then be caused by the opening/closing part 252 (352) to release the holding of the sample container 100. To be specific, the hand part 251 (351) is configured to set the sample container 100 into a sample setting part 255a (355a) that has been moved by the sample container moving part 255 (355) to a sample setting position 610 (710)(see FIG. 2). Note that as shown in FIG. 2, the first loading position 43a and the sample setting position 610 coincide with each other when viewed in a plan view. Also, the second loading position 43b and the sample setting position 710 coincide with each other when viewed in a plan view.

As shown in FIG. 3, the opening/closing part 252 (352) is configured to cause, based on the dynamics of an air cylinder 252a (352a), the hand part 251 (351) to open and close so as to hold a sample container 100.

The vertically moving part 253 (353) is configured to move, based on the dynamics of a stepping motor 253a (353a), the hand part 251 (351) along a rail 253b (353b) in the vertical directions (the arrow Z1 and Z2 directions).

The agitator 254 (354) is configured to move the hand part 251 (351) in the vertical directions (the arrow Z1 and Z2 directions) in a swinging manner based on the dynamics of a stepping motor that is not shown.

As shown in FIGS. 1 and 3, the sample container moving part 255 (355) has the sample setting part 255a (355a), and is capable of moving the sample setting part 255a (355a) to predetermined positions in accordance with operations performed during a measurement process. To be specific, the sample container moving part 255 (355) is capable of disposing the corresponding sample setting part in the aspirating position 600 (700) shown in FIG. 2, and disposing the corresponding sample setting part in the sample setting position 610 (710) shown in FIG. 2.

The bar code reader 256 (356) is configured to read a bar code 100b (shown in FIG. 4) affixed to each sample container 100. The bar code 100b of each sample container 100 is uniquely assigned to the sample therein, and used to manage analysis results of each sample.

The fixedly holding part 26 (36) is configured to fixedly hold a sample container 100 having been moved to the aspirating position 600 (700). To be specific, as shown in FIG. 2, the fixedly holding part 26 (36) has a pair of chuck parts 261 (361). The pair of chuck parts 261 (361) are configured to move closer toward each other so as to hold the sample container 100 therebetween.

As shown in FIGS. 2 and 3, the sample transporting apparatus 4 includes: a rack feeder 41 capable of feeding a plurality of racks 101 each accommodating sample containers 100 that contain unanalyzed samples; a second rack storage 42 capable of storing a plurality of racks 101 each accommodating sample containers 100 that contain samples having been analyzed; a rack transporter 43 for horizontally and rectilinearly moving a rack 101 in the arrow X1 and X2 directions; a bar code reader 44; a presence/absence detection sensor 45 for detecting presence or absence of a sample container 100; a rack transfer part 46 for transferring a rack 101 to the inside of the second rack storage 42; and a remaining amount detector 47 (see FIG. 2) for detecting a remaining amount of the sample contained in a sample container 100.

The rack feeder 41 has a rack sending out part 411, and is configured to send out racks 101, which the rack feeder 41 is holding, onto a below-described transporting part 431 of the rack transporter 43 one by one, through movement of the rack sending out part 411 in the arrow Y2 direction. The rack sending out part 411 is configured to be driven by a stepping motor (not shown) provided below the rack feeder 41. Further, the rack feeder 41 has a restricting portion 412 (see FIG. 3) near the rack transporter 43, and is configured to restrict, by the restricting portion 412, the movement of the racks 101 such that once a rack 101 is pushed onto the rack transporter 43, the rack 101 does not return to the inside of the rack feeder 41.

The second rack storage 42 is disposed between the feeding position 43d, to which a rack 101 is fed by the rack feeder 41, and a below-described first rack storage 432. The second rack storage 42 is configured to receive and store a rack 101 that has been pushed out of the rack transporter 43 in the Y1 direction by the rack transfer part 46. The second rack storage 42 has a restricting portion 421 (see FIG. 3) near the rack transporter 43, and is configured to restrict, by the restricting portion 421, the movement of the racks 101 such that once a rack 101 is moved to the inside of the second rack storage 42, the rack 101 does not return to the rack transporter 43. As shown in FIG. 2, the rack 101 is transferred to the second rack storage, at a transfer position 43e (indicated in FIG. 2 by dotted lines in the form of a rack) that is located between the first loading position 43a and the second loading position 43b.

As shown in FIG. 2, the rack transporter 43 has the transporting part 431 and the first rack storage 432. The rack transporter 43 is configured to transport a rack 101 that has been sent out of the rack feeder 41, thereby disposing the rack 101 in a predetermined position. The transporting part 431 of the rack transporter 43 is configured to be able to transport two racks 101 separately, in both a forward direction (X1 direction) and a reverse direction (X2 direction). The forward direction is a direction from the rack feeder 41 side to the first rack storage 432 side, and the reverse direction is a direction from the first rack storage 432 side to the rack feeder 41 side.

As shown in FIG. 2, the transporting part 431 is linearly provided so as to extend along the X direction. The transporting part 431 is configured to transport, on a transporting path having a width that allows only one rack 101 at a time to travel through, racks 101 in both the X1 and X2 directions. The transporting part 431 is configured to be able to: transport sample containers 100 held in a rack 101 to the first loading position 43a, the second loading position 43b, and a sample detection position 43c; receive a rack 101 from the rack feeder 41, at the feeding position 43d (indicated in FIG. 2 by dotted lines in the form of a rack); transport a rack 101 to the transfer position 43e (indicated in FIG. 2 by dotted lines in the form of a rack); and transport a rack 101 to a below-described standby position 43f (indicated in FIG. 2 by dotted lines in the form of a rack) of the first rack storage 432. As will hereinafter be described in detail, the transporting part 431 is formed to be continuously integrated with the first rack storage 432. Accordingly, the transporting part 431 is capable of transporting a rack 101 in the forward direction (X1 direction) to the first rack storage 432. The transporting part 431 is also capable of transporting a rack 101 that has temporarily been in a standby state in the first rack storage 432, to the first loading position 43a and to the second loading position 43b. The first loading position 43a and the second loading position 43b are located between the rack feeder 41 and the first rack storage 432. At the sample detection position 43c, the presence/absence detection sensor 45 is capable of confirming presence or absence of a sample container 100, the bar code reader 44 is capable of reading the bar code 100b of the sample container 100 (see FIG. 4), and the remaining amount detector 47 is capable of confirming a remaining sample amount in the sample container 100. As shown in FIG. 2, the first loading position 43a is located farther, in the forward direction (X1 direction), than the end of the forward direction side of the second rack storage 42. In this manner, the first loading position 43a is located farther, in the forward direction, than the end of the forward direction (X1 direction) side of the transfer position 43e.

Figure 6:
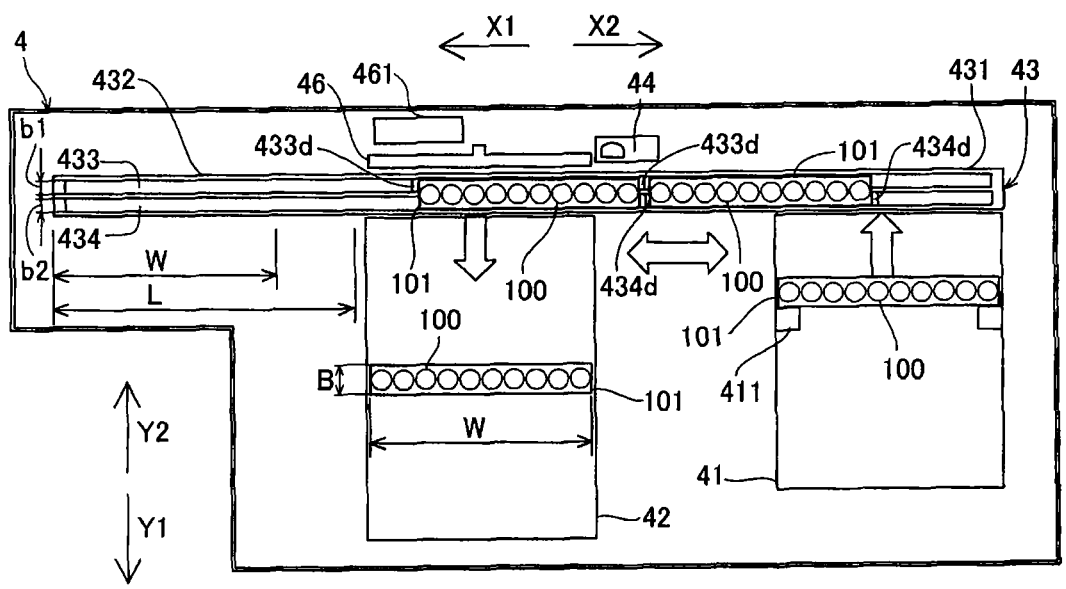
FIG. 6 is a plan view illustrating the sample transporting apparatus of the blood analyzer according to the embodiment shown in FIG. 1.

In the present embodiment, the first rack storage 432 is provided by linearly extending the transporting part 431 in the forward direction (X1 direction). The first rack storage 432 is formed so as to be continuously integrated with the transporting part 431. As shown in FIG. 6, the first rack storage 432 is provided in an area that is farther, in the forward direction (X1 direction), than the end of the forward direction (X1 direction) side of the second rack storage 42 and than the first loading position 43a, and has a length L that allows at least one rack 101 to be disposed on the first rack storage 432. The first rack storage 432 is configured to allow a rack 101 to be disposed in the standby position 43f (indicated in FIG. 2 by dotted lines in the form of a rack), and accordingly, the first rack storage 432 allows the rack 101 to temporarily stay withdrawn therein until it is determined whether or not retesting of measured samples of the rack 101 is necessary.

Figure 4:
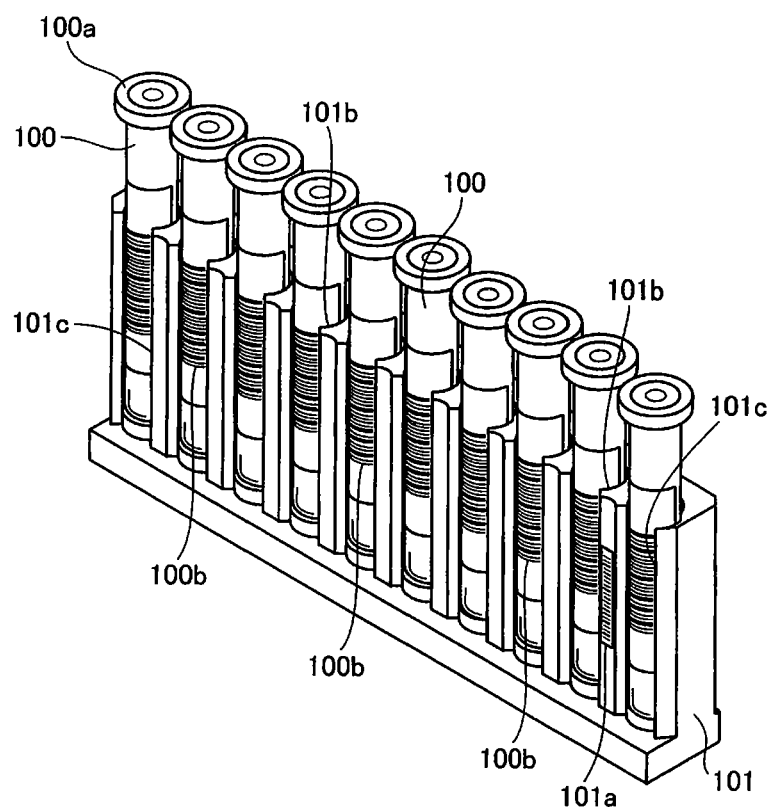
FIG. 4 is a perspective view showing a rack and sample containers of the blood analyzer according to the embodiment shown in FIG. 1.

FIGS. 5A to 5C show positional relationships among the transporting part 431, the first rack storage 432, the first loading position 43a, the second loading position 43b, the sample detection position 43c, the feeding position 43d, the transfer position 43e, and the standby position 43f. In FIGS. 5A to 5C, each sample container 100 held by racks 101 is indicated by an encircled number. As shown in FIG. 4, each rack 101 is capable of holding ten sample containers 100 at the maximum. As shown in FIG. 5A, the sample containers 100 held by each rack 101 are removed therefrom one by one at the first loading position 43a and the second loading position 43b, and then loaded into the measurement units. Also, for each sample container 100 held by the rack 101, detection of presence or absence of the sample therein, reading of the bar code thereof, and detection of a remaining sample amount therein are performed at the sample detection position 43c.

Further, in the present embodiment, as shown in FIG. 5B, in the case where two racks 101 are placed on the transporting part 431, the transporting part 431 allows four sample containers 100 (the seventh to tenth sample containers 100) from among the sample containers 100 held by a rack 101 preceding the following rack (preceding rack 101), to be disposed at the second loading position 43b when the following rack (subsequent rack) 101 is disposed at the feeding position 43d. Accordingly, even in the case where two racks are placed on the transporting part 431, all the samples of the preceding rack 101 can be transported to the first loading position 43a, and four samples (the seventh to tenth samples) thereof can be transported to the second loading position 43b. Further, as shown in FIG. 5C, when the preceding rack 101 is disposed in the standby position 43f of the first rack storage 432, four samples (the eleventh to fourteenth samples) held by the subsequent rack 101 can be disposed at the first loading position 43a so as to allow the first measurement unit 2 to measure (and retest) these four samples. Accordingly, even when two racks are placed on the transporting part 431 and the first rack storage 432, four (the eleventh to fourteenth) samples held by the subsequent rack 101 can be transported to the first loading position 43a, and also, all the samples (ten samples) held by the subsequent rack 101 can be transported to the second loading position 43b. Thus, even when two racks are placed on the rack transporter 43 (i.e., on the transporting part 431 or on both the transporting part 431 and the first rack storage 432), at least four samples of each of the preceding rack 101 and the subsequent rack 101 can be measured (and retested) by using both the measurement units.

Figure 7:
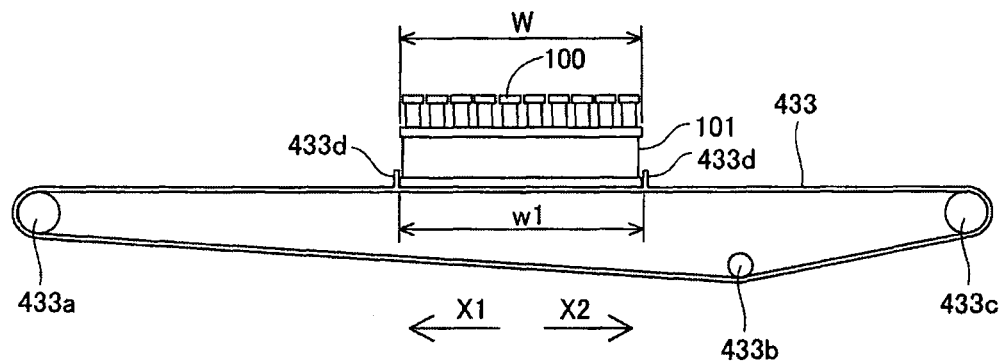
FIG. 7 is a side view illustrating the sample transporting apparatus of the blood analyzer according to the embodiment shown in FIG. 1.
Figure 8:
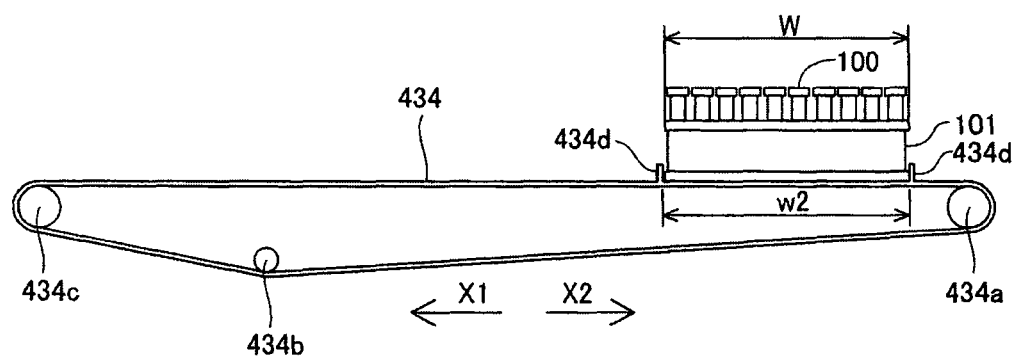
FIG. 8 is a side view illustrating the sample transporting apparatus of the blood analyzer according to the embodiment shown in FIG. 1.

As shown in FIG. 6, the transporting part 431 of the rack transporter 43 has two belts that are a first belt 433 and a second belt 434 capable of moving independently of each other. A width b1 of the first belt 433 in the arrow Y1 direction and a width b2 of the second belt 434 in the arrow Y2 direction are each equal to or smaller than the half of a width B of a rack 101 in the arrow Y1 and Y2 directions. Accordingly, the first belt 433 and the second belt 434 can be arranged in parallel to each other within the width B of the rack 101, so as not to be displaced from the width B when the transporting part 431 transports the rack 101. Further, as shown in FIGS. 7 and 8, the first belt 433 and the second belt 434 are each formed in an annular shape, and are provided so as to be wound around rollers 433a to 433c and rollers 434a to 434c, respectively. The outer periphery of the first belt 433 has two protrusions 433d formed thereon and the outer periphery of the second belt 434 has two protrusions 434d formed thereon, such that an interval between the protrusions 433d and an interval between the protrusions 434d have an inner width w1 (see FIG. 7) and an inner width w2 (see FIG. 8), respectively, which are both slightly greater (e.g., by approximately 1 mm) than a width W of the rack 101 in the arrow X1 and X2 directions. The first belt 433 is configured to move, when holding the rack 101 between the protrusions 433d, the rack 101 in the arrow X1 or X2 direction as a result of being moved around the rollers 433a to 433c by a stepping motor 433e (see FIG. 3). Also, the second belt 434 is configured to move, when holding the rack 101 between the protrusions 434d, the rack 101 in the arrow X1 or X2 direction as a result of being moved around the rollers 434a to 434c by a stepping motor 434e (see FIG. 3). The first belt 433 and the second belt 434 are configured to be able to move racks 101, respectively, and independently of each other on the transporting part 431. As a result of the stepping motor 433e and the stepping motor 434e (see FIG. 3) being controlled by a below-described control section 51, the transportation of the racks 101 by the transporting part 431 is controlled.

In the present embodiment, as shown in FIG. 6, the first belt 433 and the second belt 434 are provided so as to be entirely wound around the transporting part 431 and the first rack storage 432 that are formed as a continuous straight line. Accordingly, the racks 101 can be sequentially transported from the end (the feeding position 43d) of the reverse direction (X2 direction) side of the transporting part 431 to the end (the standby position 43f) of the forward direction (X1 direction) side of the first rack storage 432.

The bar code reader 44 is configured to read the bar code 100b of each sample container 100 shown in FIG. 4 and a bar code 101a affixed to each rack 101. The bar code reader 44 is configured to read the bar code 100b of a target sample container 100 accommodated in a rack 101 while the target sample container 100 is being horizontally rotated by a rotator (not shown) without being removed from the rack 101. Accordingly, even in the case where the bar code 100b affixed to the sample container 100 is located at the opposite side to the bar code reader 44, the bar code 100b can be caused to face the bar code reader 44. Note that the bar code 101a is uniquely assigned to each rack 101, and used for, e.g., managing analysis results of the samples. Bar code information obtained by the bar code reader 44 is transmitted to the control apparatus 5, and checked with analysis orders that specify analysis items and the like for each sample. The measurement units are configured to perform, based on the analysis orders, measurement on each sample for predetermined analysis items.

The presence/absence detection sensor 45 has a curtain-like contact segment 451 (see FIG. 3), a light emitting element for emitting light (not shown), and a light receiving element (not shown). The presence/absence detection sensor 45 is configured such that the contact segment 451 is bent when contacted by a detection subject, and as a result, the light emitted from the light emitting element is reflected by the contact segment 451 and then incident on the light receiving element. Accordingly, when a sample container 100 which is accommodated in a rack 101 and which is a detection subject passes below the presence/absence detection sensor 45, the contact segment 451 is bent by the sample container 100. As a result, the presence of the sample container 100 can be detected.

A rack transfer part 46 is provided laterally to the transporting part 431. To be specific, the rack transfer part 46 is disposed so as to be opposed to the second rack storage 42 while having the transporting part 431 arranged therebetween, and is configured to horizontally move in the arrow Y1 direction. The rack transfer part 46 is configured to push, by horizontally moving in the arrow Y1 direction, a rack 101 that is placed, on the rack transporter 43, in a transfer position 43e located between the second rack storage 42 and the rack transfer part 46, toward the second rack storage 42 side. The rack transporter 43 includes a motor 461 for driving the rack transfer part 46. As a result of the motor 461 being controlled by the below-described control section 51, the transferring of the rack 101 by the rack transfer part 46 is controlled.

The remaining amount detector 47 has a light emitter and a light receiver that are not shown, and has a function to detect a remaining amount of a sample contained in a sample container 100 disposed in the sample detection position 43c (see FIG. 2). A height up to which the light emitted by the light emitter reaches is set to be equivalent to a liquid level of a predetermined amount of sample contained in a sample container 100 (necessary amount for the measurement to be performed once). The remaining amount detector 47 is configured to detect, when the light receiver has received the light, that the remaining sample amount is less than the predetermined amount. Note that the remaining amount detector 47 is not shown in FIG. 3.

Figure 9:
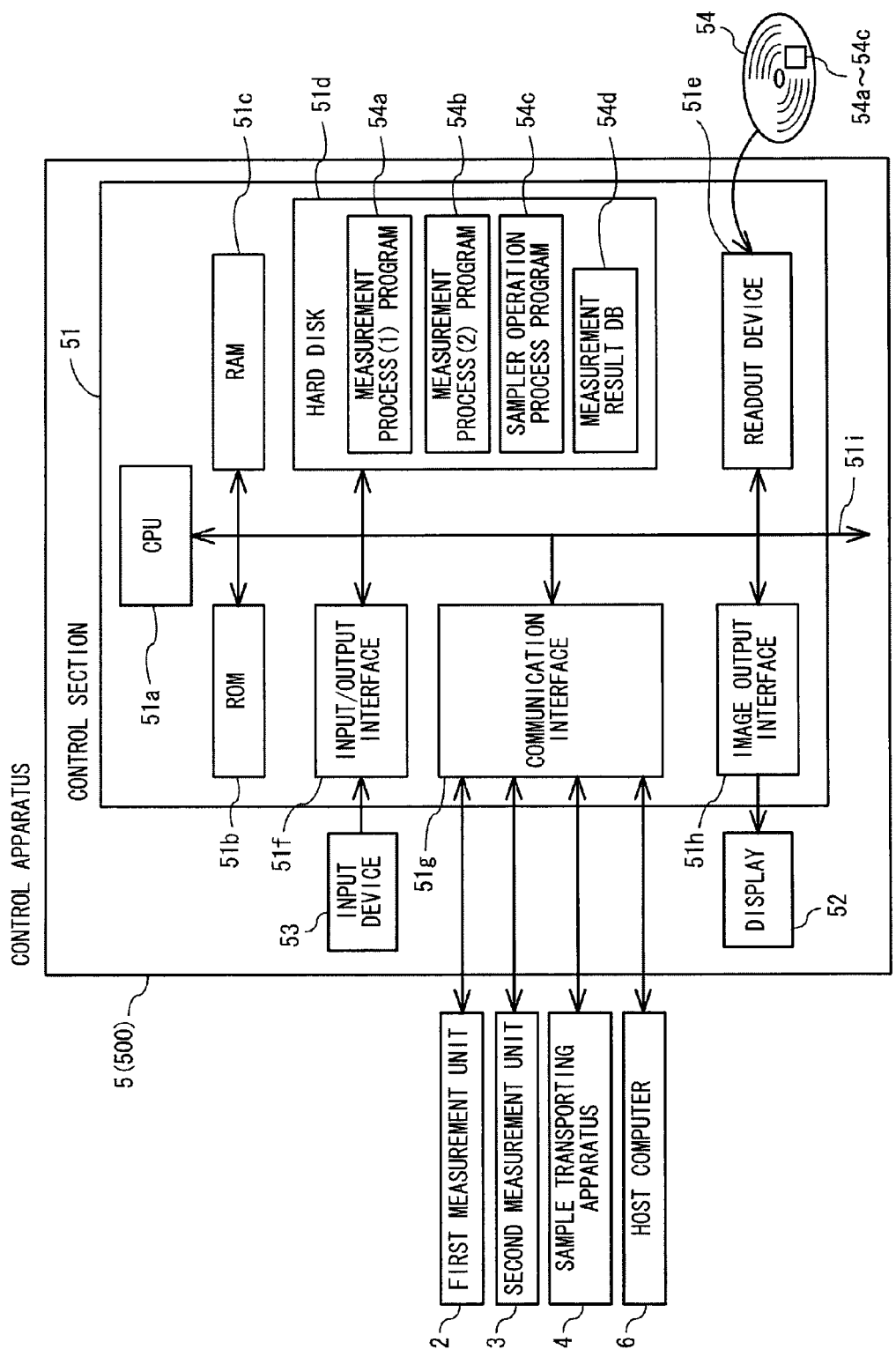
FIG. 9 is a block diagram illustrating a control apparatus of the blood analyzer according to the embodiment shown in FIG. 1.

As shown in FIGS. 1, 2 and 9, the control apparatus 5 is structured as a personal computer (PC) or the like. The control apparatus 5 includes: a control section 51 (see FIG. 9) including a CPU, ROM, RAM and the like; a display 52; and an input device 53. The display 52 is provided so as to display analysis results and the like that are obtained by analyzing digital signal data transmitted from the first measurement unit 2 and the second measurement unit 3.

As shown in FIG. 9, the control apparatus 5 is structured as a computer 500 of which the main components are the control section 51, the display 52, and the input device 53. The main components of the control section 51 are a CPU 51a, a ROM 51b, a RAM 51c, a hard disk 51d, a readout device 51e, an input/output interface 51f, a communication interface 51g, and an image output interface 51h. The CPU 51a, ROM 51b, RAM 51c, hard disk 51d, readout device 51e, input/output interface 51f, communication interface 51g, and the image output interface 51h are connected to each other via a bus 51i.

The CPU 51a is capable of executing computer programs stored in the ROM 51b and computer programs loaded into the RAM 51c. The computer 500 acts as the control apparatus 5 through execution, by the CPU 51a, of application programs 54a, 54b and 54c that are described below.

The ROM 51b is structured as a mask ROM, PROM, EPROM, EEPROM or the like, and stores computer programs to be executed by the CPU 51a and stores data to be used by the computer programs.

The RAM 51c is structured as an SRAM, DRAM or the like. The RAM 51c is used for reading computer programs stored in the ROM 51b and the hard disk 51d. The RAM 51c is used as a work area for the CPU 51a when the CPU 51a executes these computer programs.

Installed in the hard disk 51d are: various computer programs to be executed by the CPU 51a, such as an operating system and application programs; and data to be used for executing these computer programs. A measurement process (1) program 54a for the first measurement unit 2, a measurement process (2) program 54b for the second measurement unit 3, and a sampler operation process program 54c for the sample transporting apparatus 4 are also installed in the hard disk 51d. Through the execution of these application programs 54a to 54c by the CPU 51a, operations of respective components of the first measurement unit 2, the second measurement unit 3, and the sample transporting apparatus 4 are controlled. Further, a measurement result database 54d is also installed in the hard disk 51d.

The readout device 51e is structured as a flexible disc drive, CD-ROM drive, DVD-ROM drive or the like. The readout device 51e is capable of reading computer programs or data, which are stored in a portable storage medium 54. The portable storage medium 54 stores therein the application programs 54a to 54c. The computer 500 is capable of reading the application programs 54a to 54c from the portable storage medium 54 to install the read application programs 54a to 54c in the hard disk 51d.

Note that the application programs 54a to 54c can be provided to the computer 500 not only via the portable storage medium 54, but also from an external device via a telecommunication line (regardless of whether wired or wireless), which external device is communicably connected to the computer 500 by the telecommunication line. For example, the application programs 54a to 54c are stored in a hard disk of a server computer on the Internet. The computer 500 can access the server computer, and download the application programs 54a to 54c from the server computer to install the application programs 54a to 54c in the hard disk 51d.

Also, an operating system that provides a graphical user interface environment, for example, Windows (registered trademark) manufactured and sold by Microsoft Corporation, is installed in the hard disk 51d. In the description below, it is assumed that the application programs 54a to 54c run on the operating system.

For example, the input/output interface 51f is configured as: a serial interface such as USB, IEEE1394 or RS-232C; a parallel interface such as SCSI, IDE or IEEE1284; or an analogue interface including a D/A converter, A/D converter and the like. The input device 53 is connected to the input/output interface 51f. A user can input data to the computer 500 by using the input device 53.

The communication interface 51g is an Ethernet (registered trademark) interface, for example. The computer 500 is capable of transmitting/receiving data to/from the first measurement unit 2, the second measurement unit 3, the sample transporting apparatus 4, and the host computer 6 via the communication interface 51g, using a predetermined communication protocol.

The image output interface 51h is connected to the display 52 that is structured with LCD, CRT or the like. Video signals corresponding to image data, which are supplied from the CPU 51a, are outputted to the display 52. The display 52 is configured to display an image (screen) in accordance with the inputted video signals.

The control section 51 having the above configuration is configured to control the first measurement unit 2, the second measurement unit 3, and the sample transporting apparatus 4 so as to measure, in a predetermined sequence, the samples in the sample containers 100 held by each rack 101. Also, the control section 51 is configured to use measurement results transmitted from the first measurement unit 2 and the second measurement unit 3 to analyze components that are analysis subjects, and obtain results of the analysis (red blood count, platelet count, amount of hemoglobin, white blood count, and the like). Further, the control section 51 is configured to determine, based on the received measurement results, whether or not it is necessary to perform retesting of the measured samples (i.e., retest determination). When retesting is determined to be necessary for a sample, the sample is transported to a measurement unit again. Then, retesting of the sample is performed.

As shown in FIG. 4, in a rack 101, ten container accommodating portions 101b are formed so as to be able to accommodate ten sample containers 100 in line. Further, the container accommodating portions 101b are each provided with an opening 101c such that the bar code 100b of each sample container 100 accommodated therein can be viewed.

Figure 10:
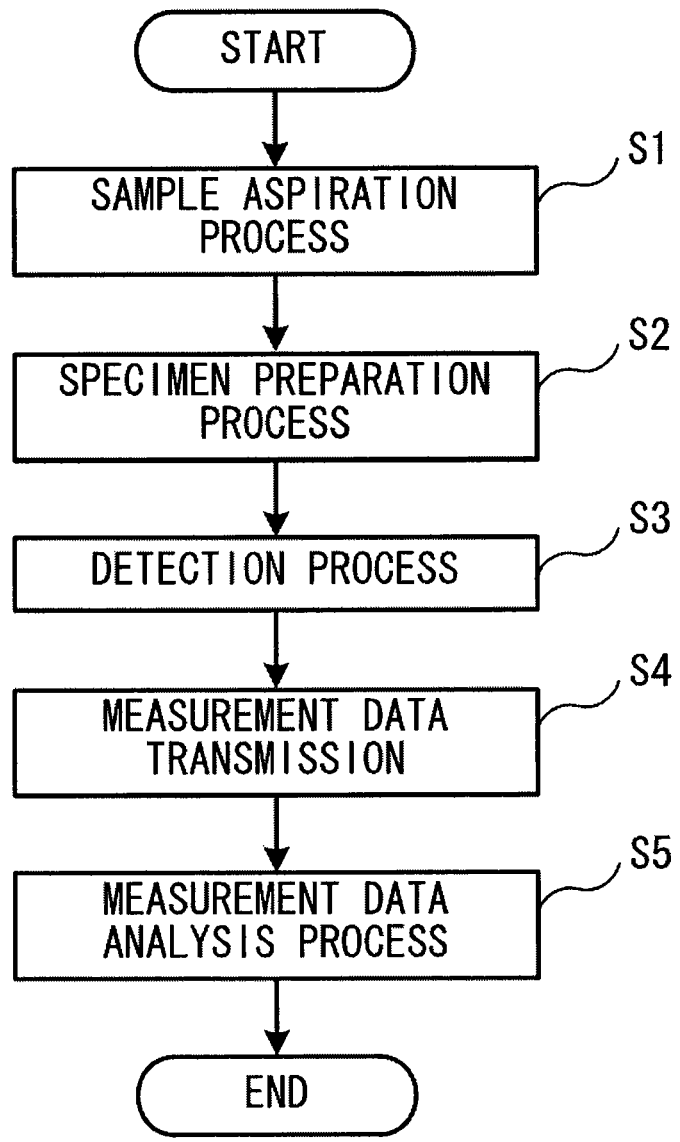
FIG. 10 is a flowchart illustrating operations that are performed in measurement processes based on measurement process programs of the blood analyzer according to the embodiment shown in FIG. 1.

FIG. 10 is a flowchart illustrating operations that are performed, in measurement processes based on the measurement process programs, by the blood analyzer according to the embodiment of the present invention. Described next with reference to FIG. 10 are operations that are performed, in measurement processes based on the measurement process programs 54a and 54b, by the blood analyzer 1 according to the present embodiment. Note that the first measurement unit 2 and the second measurement unit 3 measure, in the same manner, components that are analysis subjects. Therefore, only a case where the first measurement unit 2 measures the components that are analysis subjects is described below, and a description of operations performed by the second measurement unit 3 in the measurement process is omitted.

First, at step S1, the sample aspirator 21 aspirates a sample from a sample container 100 having been transported to the aspirating position 600 (see FIG. 2). Then, at step S2, a detection specimen is prepared from the aspirated sample by the specimen preparation section 22. At step S3, the detector 23 detects, from the detection specimen, the components that are analysis subjects. Then, at step S4, measurement data is transmitted from the first measurement unit 2 to the control apparatus 5. Thereafter, at step S5, the control section 51 analyzes, based on the measurement data transmitted from the first measurement unit 2, the components that are analysis subjects. The analysis of the sample is completed at step S5, and the operations end.

Figure 11:
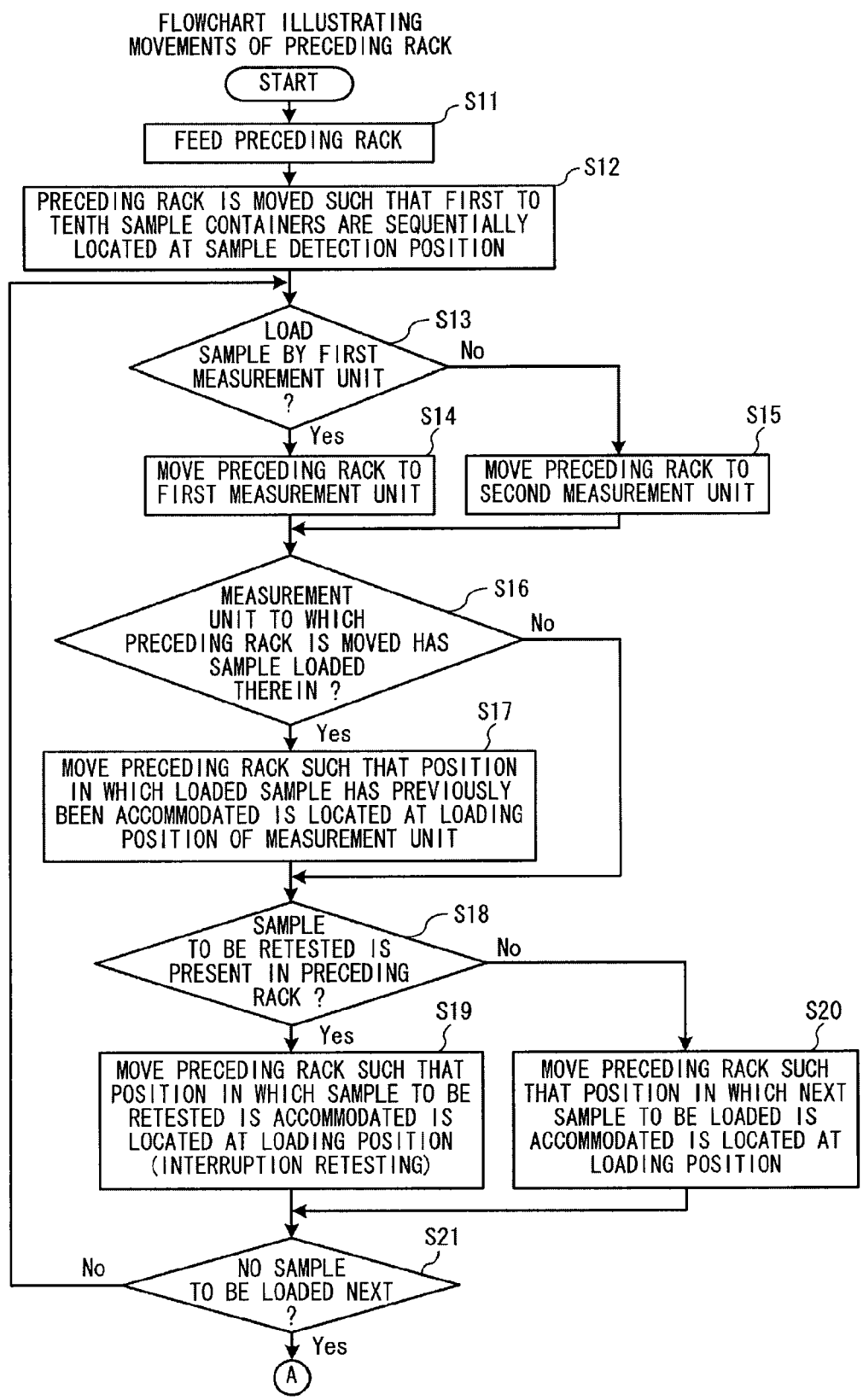
FIG. 11 is a flowchart illustrating movements of a preceding rack that is transported by the sample transporting apparatus of the blood analyzer according to the embodiment shown in FIG. 1.
Figure 12:
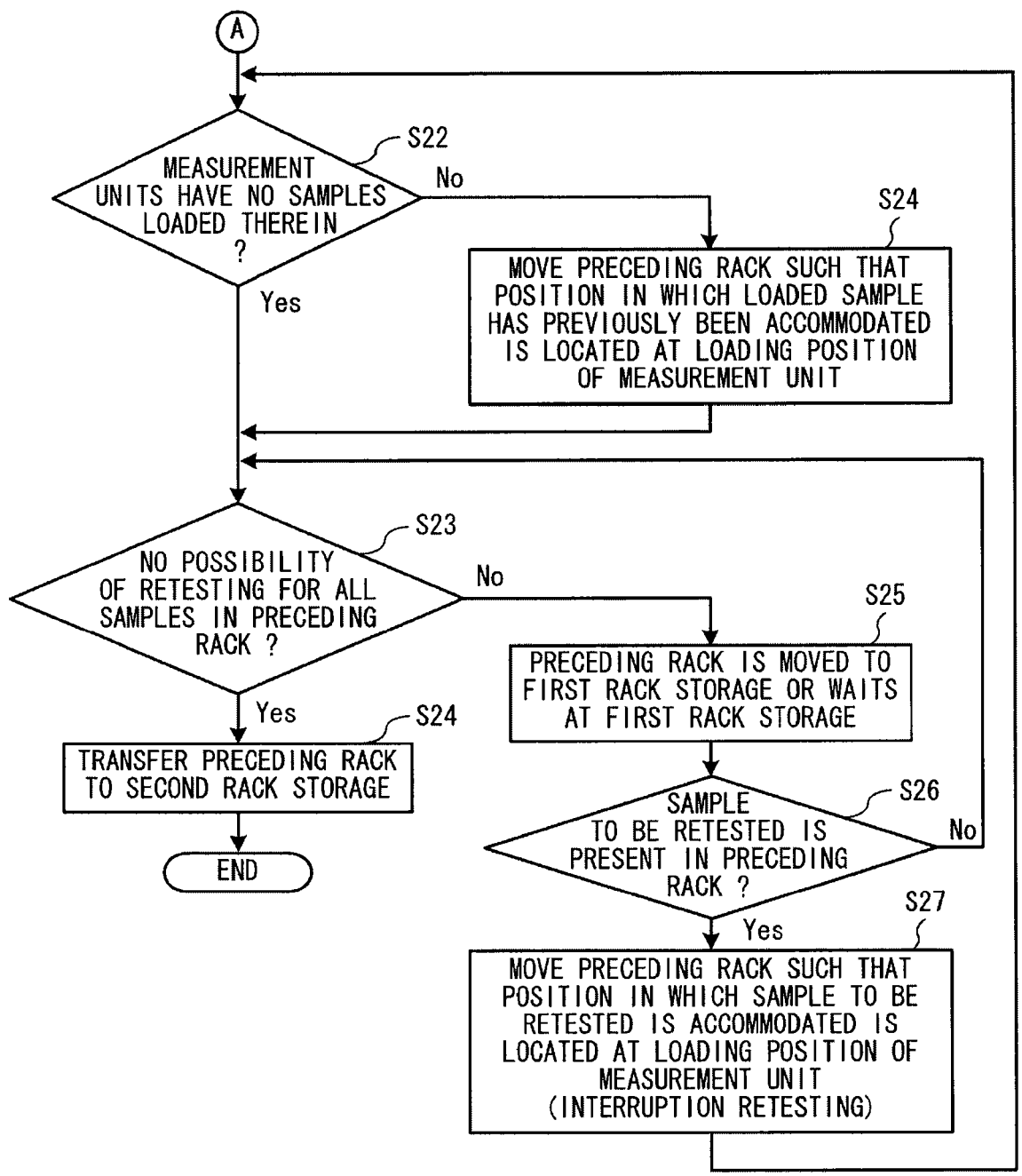
FIG. 12 is a flowchart illustrating movements of the preceding rack that is transported by the sample transporting apparatus of the blood analyzer according to the embodiment shown in FIG. 1.
Figure 13:
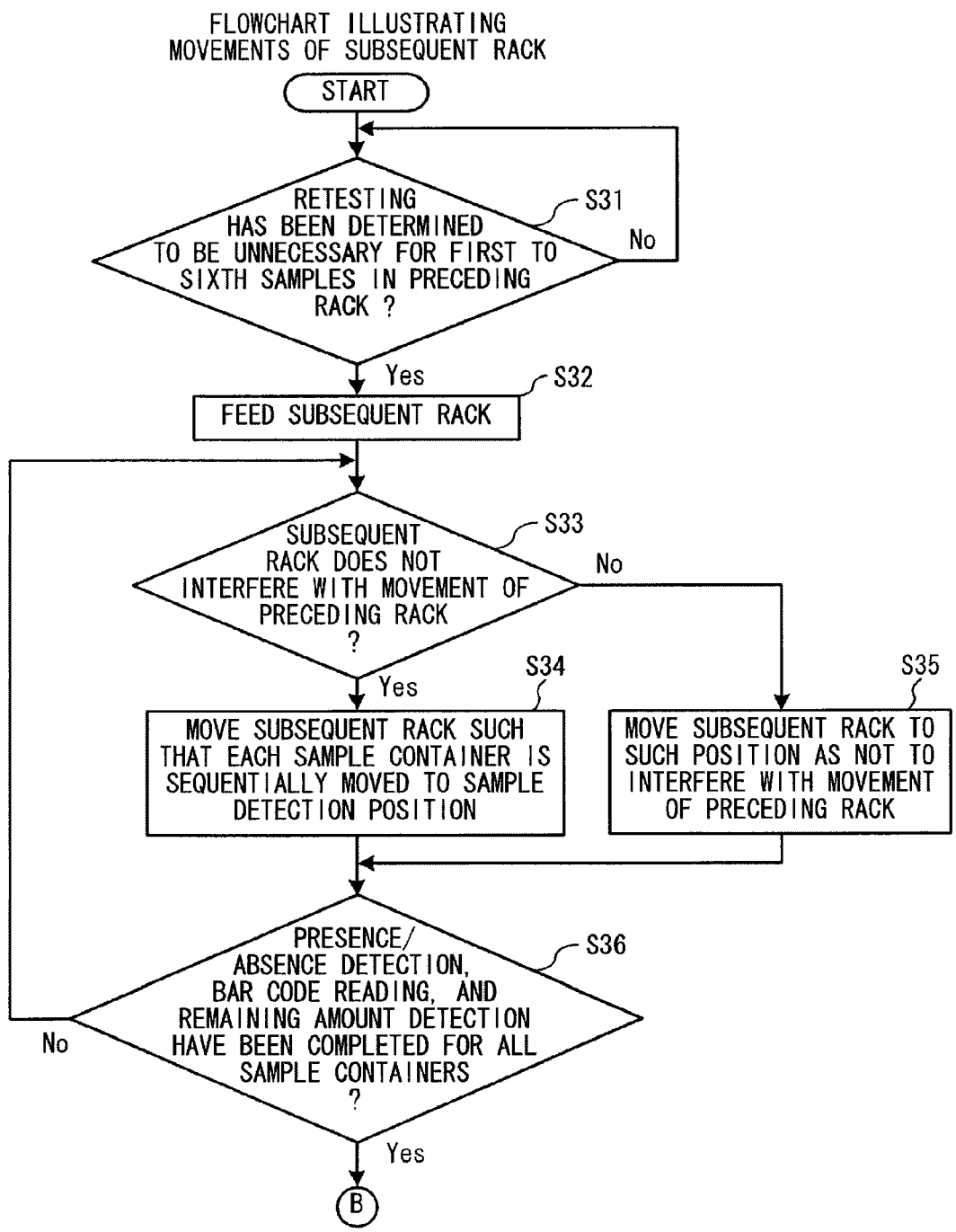
FIG. 13 is a flowchart illustrating movements of a subsequent rack that is transported by the sample transporting apparatus of the blood analyzer according to the embodiment shown in FIG. 1.
Figure 14:
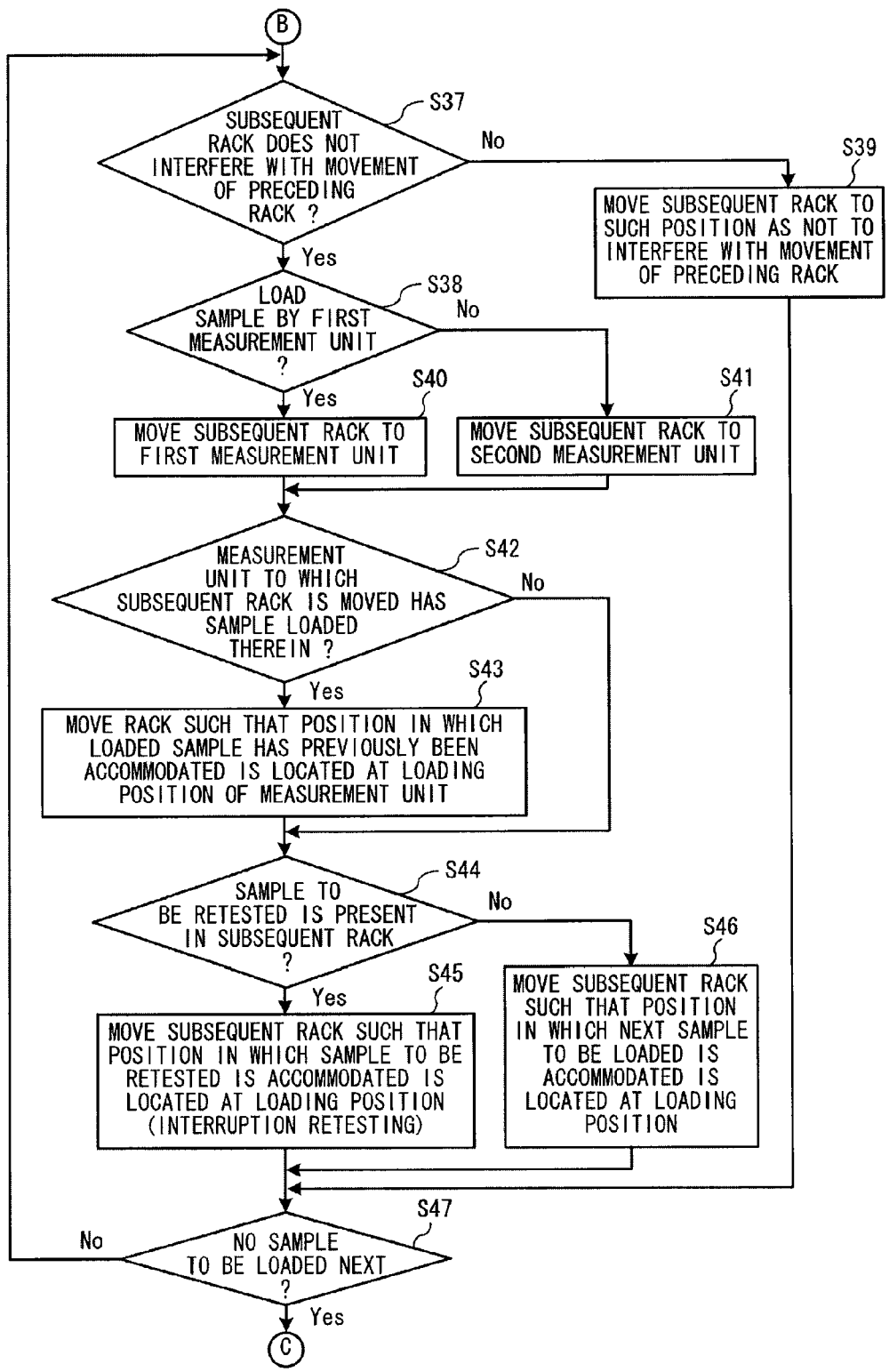
FIG. 14 is a flowchart illustrating movements of the subsequent rack that is transported by the sample transporting apparatus of the blood analyzer according to the embodiment shown in FIG. 1.
Figure 15:
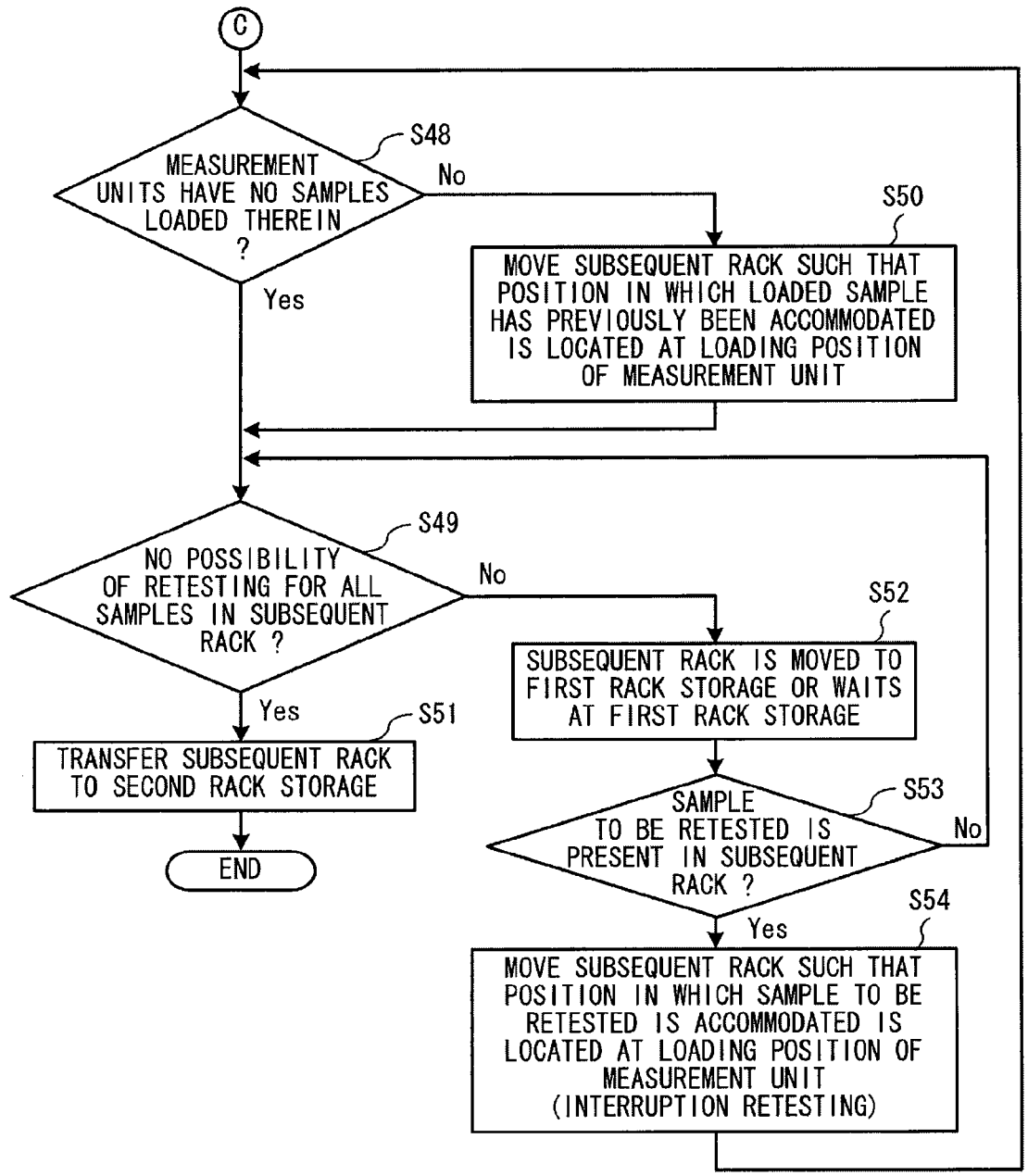
FIG. 15 is a flowchart illustrating movements of the subsequent rack that is transported by the sample transporting apparatus of the blood analyzer according to the embodiment shown in FIG. 1.

FIGS. 11 and 12 show a flowchart illustrating movements of a preceding rack that is transported by the sample transporting apparatus of the blood analyzer according to the embodiment of the present invention. FIGS. 13 to 15 show a flowchart illustrating movements of a subsequent rack that is transported by the sample transporting apparatus of the blood analyzer according to the embodiment of the present invention. FIGS. 16 to 21 each show positional relationships between sample containers and each position in the blood analyzer according to the embodiment of the present invention. Described next with reference to FIGS. 11, 12, and 16 to 20 are movements of the preceding rack 101 that is transported by the sample transporting apparatus 4 of the blood analyzer 1 according to the present embodiment. Here, referred to as the preceding rack 101 is a rack 101 that has been sent out from the rack feeder 41 to the rack transporter 43 in advance of another rack, and referred to as the subsequent rack 101 is a rack 101 which has been sent out to the rack transporter 43 and which follows the preceding rack 101 already present on the rack transporter 43 (i.e., on the transporting part 431 or on the first rack storage 432). In the blood analyzer 1 according to the present embodiment, the first measurement unit 2, the second measurement unit 3, and the sample transporting apparatus 4 operate in cooperation with each other based on the measurement process (1) program 54a, the measurement process (2) program 54b, and the sampler operation process program 54c. Accordingly, each rack 101 moves in a complicated manner in accordance with an operation state, analysis items, and the like. Hereinafter, only an example of typical movements of the racks is described without providing detailed descriptions.

First, as shown in FIG. 11, when the blood analyzer 1 is started by a user, the sample transporting apparatus 4 is initialized at step S11. Here, the protrusions 433d of the first belt 433 are moved to predetermined positions. These positions are set as original positions of the first belt 433. The two protrusions 433d are moved to positions corresponding to the feeding position 43d. Then, a preceding rack 101 holding the first to tenth sample containers 100 is fed between the two protrusions 433d of the first belt 433. At this point, the preceding rack 101 is, as shown in STATE 1 of FIG. 16, disposed in the feeding position 43d.

At step S12 (see STATE 2 of FIG. 16), the preceding rack 101 is moved in the direction of the first measurement unit 2

(in the forward direction). Then, at the sample detection position 43c, the presence/absence detection sensor 45 detects presence or absence of the first sample container 100 accommodated in the preceding rack 101; the bar code reader 44 reads the bar code 100b thereof; and the remaining amount detector 47 detects a remaining amount of the sample therein. Similarly, as shown in STATE 3 of FIG. 16, the second to tenth sample containers 100 are sequentially disposed at the sample detection position 43c, whereby the presence/absence detection, the reading of the bar code 100b, and the detection of the remaining sample amount are performed for all the sample containers 100 held by the preceding rack 101. Here, detection results obtained by the presence/absence detection sensor 45 and the remaining amount detector 47, and bar code information read by the bar code reader 44, are transmitted to the host computer 6 via the control apparatus 5 at any time as necessary.

Figure 16:
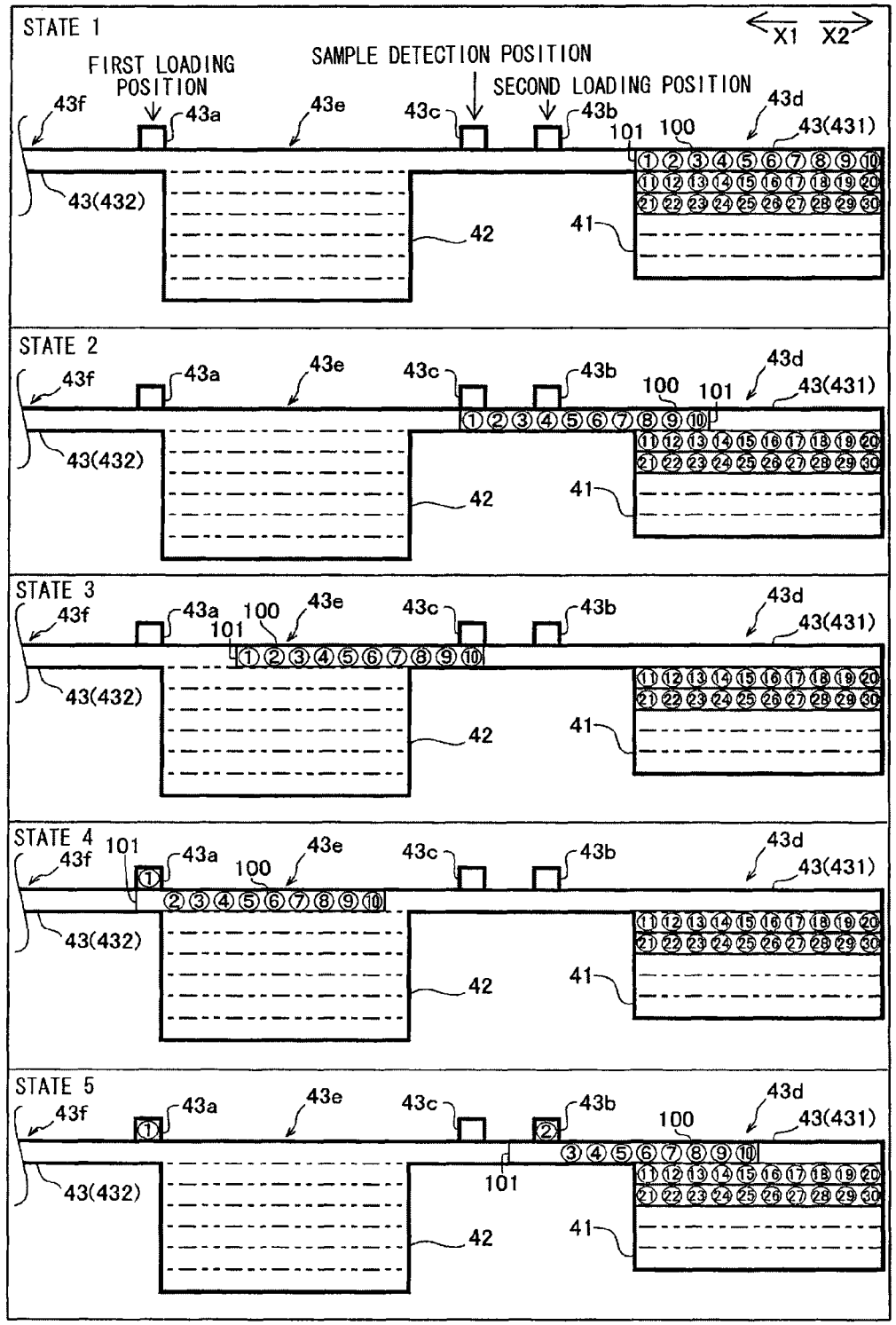
FIG. 16 shows positional relationships between sample containers accommodated in racks and each position in the blood analyzer according to the embodiment shown in FIG. 1.

At step S13, the control section 51 of the control apparatus 5 determines whether or not to perform sample loading using the first measurement unit 2. Here, the samples held by the rack are, in principle, sequentially loaded starting from the sample held at the end of the forward direction (X1 direction) side of the preceding rack 101. To be specific, the samples are loaded in order of the numbers that are assigned to the sample containers 100 as shown in FIG. 16. Further, the loading of the samples is started by the first measurement unit 2, preferentially. Accordingly, in principle, in the case where below-described interruption retesting is not performed, odd-numbered sample containers 100 are loaded into the first measurement unit 2, and even-numbered sample containers 100 are loaded into the second measurement unit 3. Based on the above principle, it is determined at step S13 whether or not the sample loading is to be performed by the first measurement unit 2. Note that a measurement sequence of the samples is determined based on, for example, the analysis orders that specify analysis items for each sample. Therefore, in practice, the measurement sequence is complex. However, the measurement sequence is simplified herein in order to facilitate the understanding of the description.

When it is determined at step S13 that the sample loading is to be performed by the first measurement unit 2, the processing proceeds to step S14, at which the preceding rack 101 is transported toward the first measurement unit 2. As shown in STATE 3 of FIG. 16, the preceding rack 101 is transported in the forward direction (X1 direction) toward the first measurement unit 2, in order for loading of the first sample container 100 to be performed. On the other hand, when it is determined at step S13 that the loading of the first sample container 100 is not to be performed by the first measurement unit 2, the processing proceeds to step S15.

Next, at step S16, the control section 51 determines whether or not the measurement unit to which the preceding rack 101 is transported has a sample loaded therein. If the measurement unit has a sample loaded therein, the processing proceeds to step S17, at which the preceding rack 101 is transported such that a position in the preceding rack 101, in which the loaded sample has previously been accommodated, is located at the loading position. Then, the loaded sample container 100 is returned to the preceding rack 101. When the measurement unit to which the preceding rack 101 is transported has no sample loaded therein, the processing proceeds to step S18. When the measurement unit has no sample loaded therein as shown in STATE 3 of FIG. 16, the processing proceeds to step S18.

At step S18, the control section 51 determines whether or not a sample to be retested is present within the sample containers 100 held by the preceding rack 101. Here, the control section 51 uses measurement results received from each measurement unit to analyze components that are analysis subjects, thereby determining whether or not to retest a sample having been measured. When a sample to be retested is present within the preceding rack 101, the processing proceeds to step S19, at which measurement of the sample to be retested cuts in to the measurement sequence. In this case, measurement of a sample to be measured at the time is rescheduled so as to be performed next or thereafter. Note that sample measurement and retest determination are performed by each measurement unit at predetermined intervals. For example, loading of a sample by a measurement unit is performed every 36 seconds, and retest determination is performed 75 seconds after the sample has been loaded into the measurement unit. In this case, a result of the retest determination is obtained after two more samples have been loaded into the measurement unit. In other words, a result of the retest determination on the first sample is obtained after the third sample has been loaded.

On the other hand, when it is determined at step S18 that a sample to be retested is not present in the preceding rack 101, the processing proceeds to step S20, at which the preceding rack 101 is transported such that a position in the preceding rack 101, in which a sample to be loaded is accommodated, is located at the loading position of the measurement unit. Accordingly, as shown in STATE 4 of FIG. 16, a position in the preceding rack 101, in which the first sample container 100 is accommodated, is located at the first loading position 43a. Then, the first sample is loaded into the first measurement unit 2.

When the first sample has been loaded, the processing proceeds to step S21, at which the control section 51 determines presence or absence of a sample to be loaded. When a sample to be loaded next is present within the preceding rack 101, the processing returns to step S13, and the loading operations are sequentially performed until there is no more sample to be loaded from the preceding rack 101. When there is no more sample to be loaded therefrom, the processing proceeds step S22. Accordingly, the above steps S13 to S21 are repeated until all the samples (ten samples) accommodated in the preceding rack 101 are loaded.

To be specific, in the case where the second sample in the preceding rack 101 is loaded, the processing proceeds to step S15 since the first sample has been loaded into the first measurement unit 2 at step S13. Then, at step S15, the preceding rack 101 is transported toward the second measurement unit 3. Thereafter, the same processing as that performed for the first sample is performed, and then the processing proceeds to step S20. Consequently, at step S20, as shown in STATE 5 of FIG. 16, a position in the preceding rack 101, in which the second sample container 100 is accommodated, is located at the second loading position 43b. Then, the second sample is loaded into the second measurement unit 3.

For the loading of the third sample, it is determined at step S13 that the third sample is to be loaded into the first measurement unit 2. Then, the processing proceeds to step S14, at which the preceding rack 101 is transported toward the first measurement unit 2. Here, since the first sample has been loaded into the first measurement unit 2 as shown in STATE 5 of FIG. 16, it is determined at step S16 that the first measurement unit 2 has a sample loaded therein. Consequently, the processing proceeds to step S17. Then, at step S17, the preceding rack 101 is transported such that a position in the preceding rack 101, in which the loaded first sample container has previously been accommodated, is located at the first loading position 43a. Next, as shown in STATE 6 of FIG. 17, the first sample (i.e., the first sample container 100) for which the measurement has been completed is returned to the preceding rack 101. When the first sample container 100 is returned to the preceding rack 101, the processing proceeds to step S18. When it is determined at step S18 that no sample to be retested is present in the preceding rack 101, the third sample container 100 is loaded into the first measurement unit 2, similarly to the first sample container 100. By repeating the above processes, the samples are loaded sequentially.

Retest determination results for samples that have been measured are obtained when the third sample container 100 has been loaded and thereafter. Hereinafter, a description is given taking, as an example, a case where retest determination is performed for the sixth sample. As shown in STATE 7 of FIG. 17, whether or not retesting of the sixth sample is necessary is determined when the second sample after the loading of the sixth sample into the second measurement unit 3 (i.e., the eighth sample), has been loaded into the second measurement unit 3.

Figure 17:
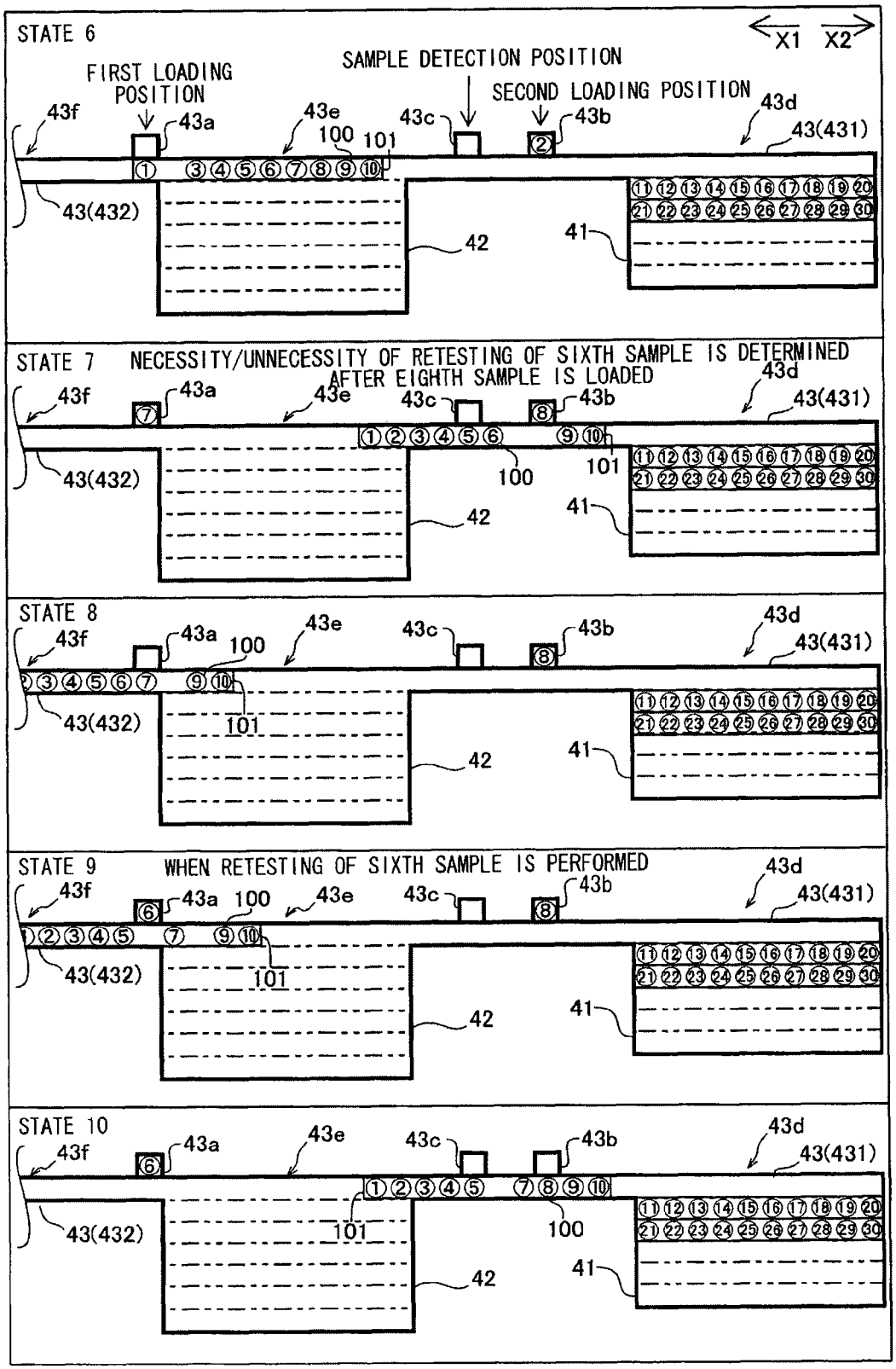
FIG. 17 shows positional relationships between the sample containers accommodated in the racks and each position in the blood analyzer according to the embodiment shown in FIG. 1.

In the case where retesting is performed for the sixth sample, when the seventh sample container 100 loaded within the first measurement unit 2 is returned to the preceding rack 101 at step S17 as shown in STATE 8 of FIG. 17, the control section 51 determines at step S18 that there is a sample to be retested. Then, as shown in STATE 9 of FIG. 17, at step S19, loading of the sixth sample that is a sample to be retested is performed in an interrupting manner before loading of the ninth sample. In this case, the measurement sequence is altered such that loading of the ninth sample is performed next or thereafter.

Subsequently, as shown in STATE 10, when the eighth sample container 100 is returned from the second measurement unit 3 to the preceding rack 101, presence or absence of a sample to be retested is determined. When there is no sample to be retested, the ninth sample is loaded into the second measurement unit 3 as shown in STATE 11 of FIG. 18.

In the case where there is no sample to be retested after STATE 11, the sixth sample container 100 for which the retesting has been performed is returned to the preceding rack 101 as shown in STATE 12, and then the tenth sample container 100 is loaded into the first measurement unit 2 as shown in STATE 13. As a result, since all the ten samples accommodated in the preceding rack 101 have been loaded into the measurement units, it is determined at step S21 of FIG. 11 that there is no sample to be loaded next. Then, the processing proceeds to step S22. Note that in STATE 12 of FIG. 18 where the sixth sample container 100 that is a subject of retesting has been returned to the preceding rack 101, the subsequent rack 101 is sent out from the rack feeder 41 to the rack transporter 43. Movements of the subsequent rack 101 will be described later.

As shown in FIG. 12, it is determined at step S22 whether or not the measurement units have loaded samples therein. When the sample containers 100 previously accommodated in the preceding rack 101 have all been returned from the measurement units, the processing proceeds to step S23. Meanwhile, as shown in STATE 13 of FIG. 18, when the tenth sample container 100 has just been loaded, the ninth and tenth sample containers 100 are in the state of having being loaded within the respective measurement units. Accordingly, the processing proceeds to step S24.

At step S24, the preceding rack 101 is transported such that positions in the preceding rack 101, in which these loaded sample containers have previously been accommodated, are located at the loading positions of the measurement units. Consequently, after the ninth sample container 100 is returned to the preceding rack 101 as shown in STATE 14 of FIG. 18, the tenth sample container 100 is also returned to the preceding rack 101 as shown in STATE 15. In this manner, all the sample containers 100 of the preceding rack 101 are returned from the measurement units to the preceding rack 101. Then, the processing proceeds to step S23 of FIG. 12.

At step S23, it is determined for all the samples accommodated in the preceding rack 101 whether or not there is a possibility of retesting. At the time of STATE 15 where the tenth sample container 100 has just been returned to the preceding rack 101, results of the retest determination for the ninth and tenth samples are yet to be obtained. Accordingly, the processing proceeds to step S25.

At step S25, the preceding rack 101 is transported in the X1 direction by the transporting part 431 to the standby position 43$f$ of the first rack storage 432. Here, as shown in STATE 16 of FIG. 19, the preceding rack 101 comes into a standby state at the standby position 43$f$. Then, at step S26 of FIG. 12, it is determined based on retest determination results whether or not a sample to be retested is present in the preceding rack 101. When there is no sample to be retested in the preceding rack 101, the processing returns to step S23, and then it is determined again for all the samples accommodated in the preceding rack 101 whether or not there is a possibility of retesting. Accordingly, steps S23, S25 and S26 are repeated until retest determination results are obtained for all the samples for which retest determination results have not been obtained yet. During this period, the preceding rack 101 stands by at the standby position 43$f$ of the first rack storage 432.

When it is determined based on the retest determination results that all the samples including the ninth and tenth samples have been retested or do not require retesting, it is determined at step S23 for all the samples in the preceding rack 101 that there is no possibility of retesting. Then, the processing proceeds to step S24. At step S24, as shown in STATE 17 of FIG. 19, the preceding rack 101 for which all the processes have been completed is transported in the reverse direction (X2 direction) toward the second rack storage 42. Then, when the preceding rack 101 is disposed at the transfer position 43$e$, the preceding rack 101 is transferred by the rack transfer part 46 to the second rack storage 42. As a result, as shown in STATE 18, the preceding rack 101 is transferred to the second rack storage 42, which is the end of all the processes for the preceding rack 101.

On the other hand, when it is determined that retesting of, for example, the tenth sample is necessary, it is determined at step S26 that a sample to be retested is present in the preceding rack 101. Then, the processing proceeds to step S27. At step S27, the tenth sample that is a sample to be retested cuts in to the measurement sequence, and in order to perform loading of the tenth sample container 100 again, the preceding rack 101 is transported to a measurement unit. Here, when the first sample in the subsequent rack 101 (i.e., the eleventh sample in the measurement sequence) is returned from the second measurement unit 3 to the subsequent rack 101 as shown in STATE 17 of FIG. 19, the preceding rack 101 is transported from the standby position 43$f$ of the first rack storage 432 to the second loading position 43$b$ as shown in STATE 19. Then, the tenth sample is loaded into the second measurement unit 3.

Figure 19:
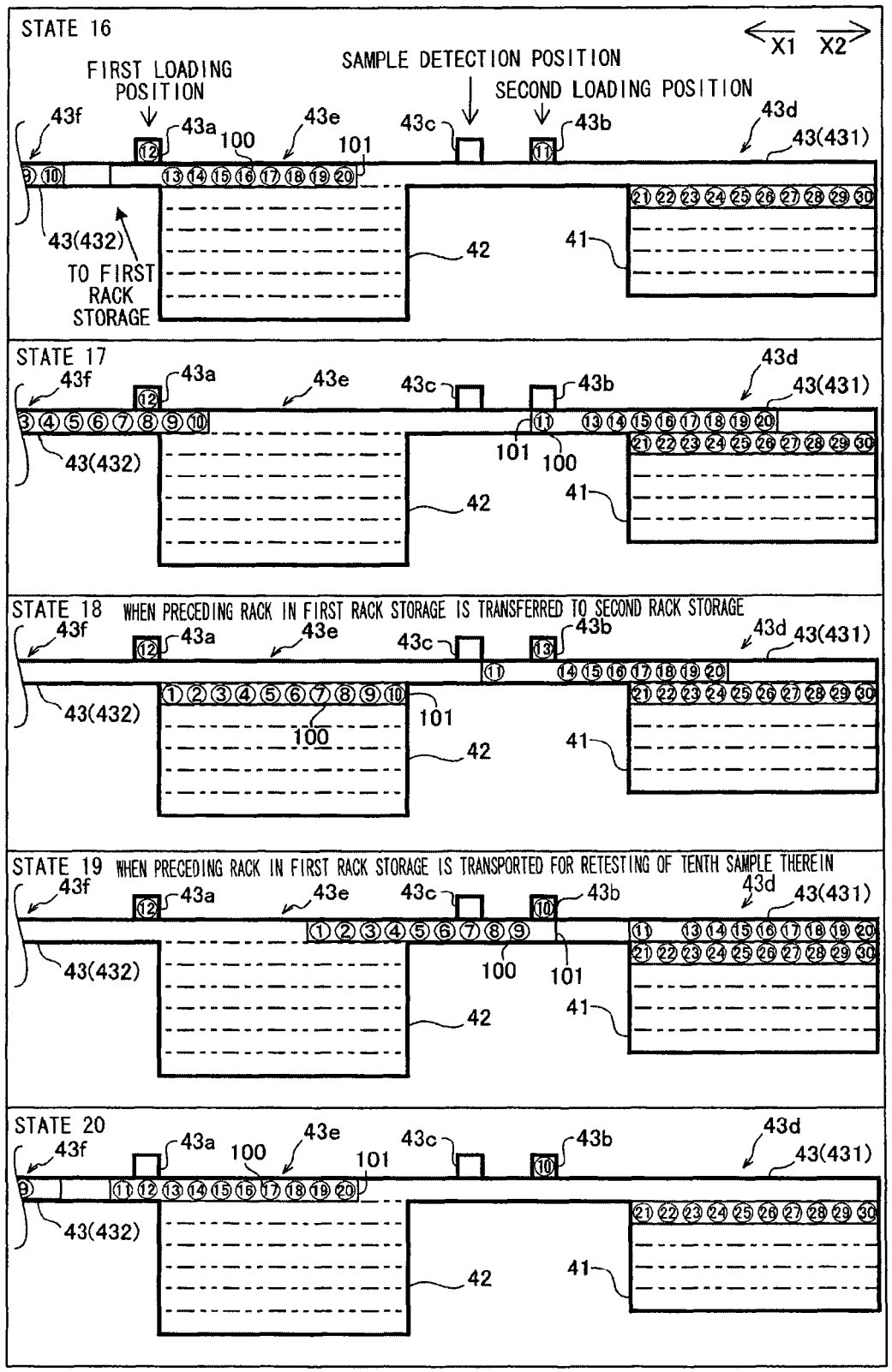
FIG. 19 shows positional relationships between the sample containers accommodated in the racks and each position in the blood analyzer according to the embodiment shown in FIG. 1.

Thereafter, as shown in STATE 20 of FIG. 19, the preceding rack 101 is transported to the standby position 43$f$ of the first rack storage 432 again and stays in a standby state until the tenth sample becomes removable from the second measurement unit 3. Thereafter, through the processes at steps S22 and S24, the tenth sample loaded within the second measurement unit 3 is returned to the preceding rack 101 as shown in STATE 21 of FIG. 20. Then, it is determined at step S23 that there is no possibility of retesting of the preceding rack 101 for which retest determination has been performed for all the samples accommodated therein, and the preceding rack 101 is transferred to the second rack storage 42 at step S24 as shown in STATE 22 of FIG. 20.

With the above, a series of movements of the preceding rack 101 transported by the sample transporting apparatus 4 end.

Described next with reference to FIGS. 13 to 21 are movements of the subsequent rack 101 that is transported by the sample transporting apparatus 4 of the blood analyzer 1 according to the present embodiment.

As shown in FIG. 13, it is determined at step S31, based on a result of the retest determination performed for each sample, whether or not retesting is not necessary for the first to sixth samples in the preceding rack 101. Note that in the present embodiment, a description is given on condition that retesting is performed only once for each sample. Therefore, retesting is determined to be unnecessary for samples that have already been retested. The determination at step S31 is repeatedly performed if there is a possibility of retesting among the first to sixth samples in the preceding rack 101. Here, when it is determined that retesting is not necessary for the first to sixth samples in the preceding rack 101, the processing proceeds to step S32, at which the subsequent rack 101 is sent out to the feeding position 43d of the rack transporter 43 as shown in STATE 23 of FIG. 20. At the time, the protrusions 434d of the second belt 434 are moved to predetermined positions, and these positions are set as original positions of the second belt 434. The two protrusions 434d are moved to positions corresponding to the feeding position 43d, and the subsequent rack 101, which holds ten sample containers 100 (the eleventh to twentieth sample containers 100), is fed between the two protrusions 434d of the second belt 434.

In the case where retesting is performed for the sixth sample of the preceding rack 101, retesting of the sixth sample is performed at step S31 in an interrupting manner between the measurement of the eighth sample and the measurement of the ninth sample, as shown in STATE 9 of FIG. 17. Accordingly, after the eighth sample having been loaded into the second measurement unit 3 is returned to the preceding rack 101 as shown in STATE 10 and the ninth sample container 100 is loaded into the second measurement unit 3 as shown in STATE 11 of FIG. 18, the sixth sample container 100 is returned from the first measurement unit 2 to the preceding rack 101 as shown in STATE 12. When the sixth sample has been returned to the preceding rack 101, it is determined at step S31 that retesting is not necessary for the first to sixth samples in the preceding rack 101. Then, the processing proceeds to step S32, at which the subsequent rack 101 is sent out to the feeding position 43d of the transporting part 431 as shown in STATE 12. As described above, as a result of the determination at step S31, the subsequent rack 101 is sent out to the transporting part 431 from the rack feeder 41 in accordance with the result of the retest determination performed for the preceding rack 101.

When the subsequent rack 101 is sent out to the transporting part 431, it is determined at step S33 whether or not the subsequent rack 101 interferes with the movement of the preceding rack 101. When the subsequent rack 101 does not interfere with the movement of the preceding rack 101, the processing proceeds to step S34, at which the subsequent rack 101 is transported to the sample detection position 43c. When the tenth sample container 100 is loaded from the preceding rack 101 into the first measurement unit 2 as shown in STATE 13 of FIG. 18, the loading of the tenth sample container 100 from the preceding rack 101 is not interfered with by the subsequent rack 101 even when the end of the X2 direction side of the subsequent rack 101 is disposed at the sample detection position 43c. Therefore, at step S34, the subsequent rack 101 is moved in the direction of the first measurement unit 2 (i.e., in the forward direction). Accordingly, at the sample detection position 43c, the presence/absence detection sensor 45 detects presence or absence of the eleventh sample container 100 accommodated in the subsequent rack 101; the bar code reader 44 reads the bar code 100b thereof; and the remaining amount detector 47 detects a remaining amount of the sample therein.

Figure 18:
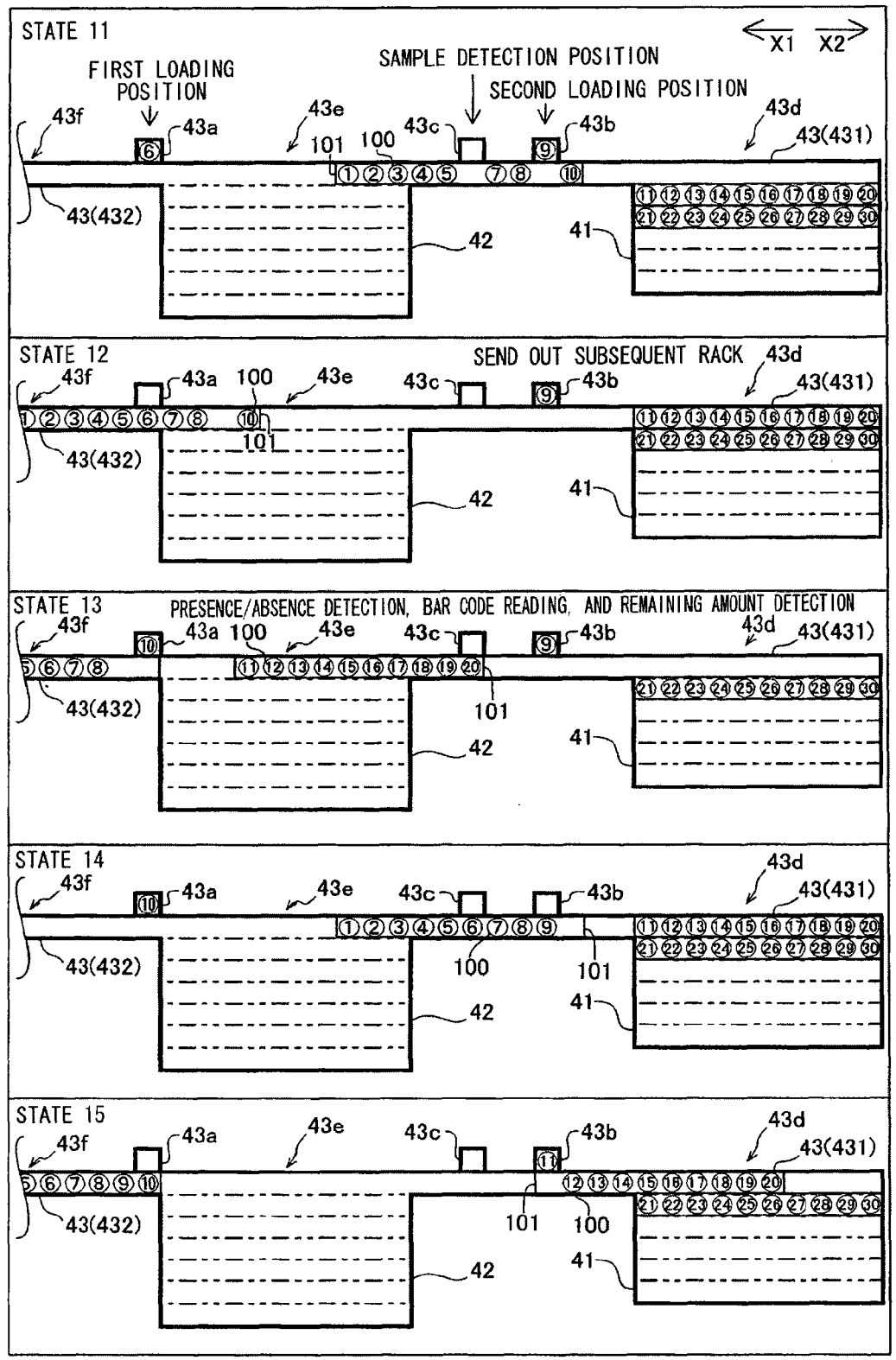
FIG. 18 shows positional relationships between the sample containers accommodated in the racks and each position in the blood analyzer according to the embodiment shown in FIG. 1.

In the case where the ninth sample container 100 is returned from the second measurement unit 3 to the preceding rack 101 as shown in STATE 14 of FIG. 18, a position in the preceding rack 101, in which the ninth sample container has previously been accommodated, is located at the second loading position 43b. In this case, since the subsequent rack 101 interferes with the movement of the preceding rack 101, the processing proceeds to step S35, at which the subsequent rack 101 is transported in the reverse direction (X2 direction) to the vicinity of the feeding position 43d of the transporting part 431, whereby the subsequent rack 101 is moved to such a position as not to interfere with the movement of the preceding rack 101.

At step S36, it is determined whether or not the presence/absence detection, bar code reading, and remaining amount detection have been completed for all the sample containers 100 (the eleventh to twentieth sample containers) of the subsequent rack 101. The processes at steps S33 to S36 are repeated until the presence/absence detection, bar code reading, and remaining amount detection have been completed for all the sample containers 100 (the eleventh to twentieth sample containers) of the subsequent rack 101. In this manner, the presence/absence detection, bar code reading, and remaining amount detection are performed for all the sample containers 100 accommodated in the subsequent rack 101, without interfering with the movement of the preceding rack 101.

Thereafter, when the presence/absence detection, bar code reading, and remaining amount detection have been completed for all the sample containers 100 (the eleventh to twentieth sample containers) of the subsequent rack 101, the processing proceeds to step S37. At step S37, it is determined whether or not the subsequent rack 101 interferes with the movement of the preceding rack 101. When the subsequent rack 101 interferes with the movement of the preceding rack 101, the processing proceeds to step S39, at which the subsequent rack 101 is transported by the transporting part 431 in the reverse direction (X2 direction) to such a position as not to interfere with the movement of the preceding rack 101. When the ninth sample container 100 is returned to the preceding rack 101 from the second measurement unit 3 as shown in STATE 14 of FIG. 18, the subsequent rack 101 interferes with the movement of the preceding rack 101. Therefore, the subsequent rack 101 is transported in the reverse direction (X2 direction) to the vicinity of the feeding position 43d of the transporting part 431, whereby the subsequent rack 101 is moved to such a position as not to interfere with the preceding rack 101. Whereas when the subsequent rack 101 does not interfere with the movement of the preceding rack 101, the processing proceeds to step S38, at which sample loading is performed. In STATE 15, the tenth sample container 100 is returned from the first measurement unit 2 to the preceding rack 101 at the first loading position 43a. In this case, the subsequent rack 101 does not interfere with the movement of the preceding rack 101. Therefore, the subsequent rack 101 is transported in the forward direction (X direction) in accordance with the movement of the preceding rack 101.

Note that the movements of the subsequent rack 101 during sample loading at steps S38 and S40 to S46 are the same as those of the preceding rack 101 indicated at steps S13 to S20 of FIG. 11. Accordingly, at steps S38, S40 and S41, after it is determined which measurement unit is to be used for the next sample loading, the subsequent rack 101 starts moving toward the measurement unit that is to perform the loading. Next, it is determined at step S42 whether or not the measurement unit to which the subsequent rack 101 is moved has a loaded sample therein. At step S43, a sample container 100 loaded within the measurement unit to which the subsequent rack 101 is moved is returned to the corresponding rack 101. Then, at steps S44 to S46, presence or absence of a sample to be retested is determined. When a sample to be retested is present in the subsequent rack 101, the retesting cuts in to the measurement sequence, and the sample container 100 to be retested is loaded into the measurement unit. Whereas when a sample to be retested is not present in the subsequent rack 101, sample loading is performed in accordance with the measurement sequence. Accordingly, as shown in STATE 15 of FIG. 18, when the preceding rack 101 is disposed at the first loading position 43a and the tenth sample container 100 is returned to the preceding rack 101, the subsequent rack 101 is disposed at the second loading position 43b and the eleventh sample container 100 (the first sample container 100 of the subsequent rack 101) is loaded into the second measurement unit 3.

Thereafter, as shown in FIG. 14, presence or absence of a sample to be loaded next is determined at step S47. If there is a sample to be loaded next, the processing proceeds to step S37, at which it is determined again whether or not the subsequent rack 101 interferes with the movement of the preceding rack 101. By repeating these steps S37 to S47, sample measurement is performed. As shown in STATE 16 of FIG. 19, when the preceding rack 101 is disposed at the standby position 43f of the first rack storage 432 and comes into a standby state for retest determination, the subsequent rack 101 is disposed at the first loading position 43a and the twelfth sample container 100 is loaded into the second measurement unit 3. Then, as shown in STATE 17, when the preceding rack 101 starts moving from the first rack storage 432, the processing proceeds to step S39, at which the subsequent rack 101 moves to such a position as not to interfere with the movement of the preceding rack 101. Here, as shown in STATE 17 and STATE 18, when the preceding rack 101 moves toward the second rack storage 42 from the first rack storage 432, the subsequent rack 101 is transported to the second loading position 43b. Then, the eleventh sample container 100 is returned to the subsequent rack 101 from the second measurement unit 3, and also, the thirteenth sample container 100 is loaded into the second measurement unit 3.

In the case where the tenth sample is to be retested, the eleventh sample container 100 is returned from the second measurement unit 3 to the subsequent rack 101 at the second loading position 43b as shown in STATE 17 so as to allow the tenth sample, which is a sample to be retested, to cut in to the measurement sequence. Then, the preceding rack 101 starts moving toward the second loading position 43b. Accordingly, at step S39 of FIG. 14, the subsequent rack 101 is transported in the reverse direction (X2 direction) to the vicinity of the feeding position 43d of the transporting part 431 such that the subsequent rack 101 is located at such a position as not to interfere with the movement of the preceding rack 101. Thereafter, as shown in STATE 19 of FIG. 19, the preceding rack 101 is transported such that a position in the preceding rack 101, in which the tenth sample container is accommodated, is moved from the standby position 43f of the first rack storage 432 to the second loading position 43b. Then, the tenth sample container 100 is loaded into the second measurement unit 3 again.

Subsequently, as shown in STATE 20, the preceding rack 101 is transported again to the standby position 43f of the first rack storage 432 and stays in a standby state until retesting of the tenth sample ends. In response to the movement of the preceding rack 101 in the forward direction (X1 direction), the subsequent rack 101 is disposed at the first loading position 43a, and the twelfth sample container 100 is returned to the subsequent rack 101. Then, the thirteenth sample container 100 is loaded from the subsequent rack 101 into the first measurement unit 2. Note that as shown in STATE 20, while the preceding rack 101 is standing by in the standby position 43f of the first rack storage 432, the eleventh to fourteenth sample containers 100 (the first to fourth containers in the subsequent rack) can be loaded into either the first measurement unit 2 or the second measurement unit 3.

Figure 20:
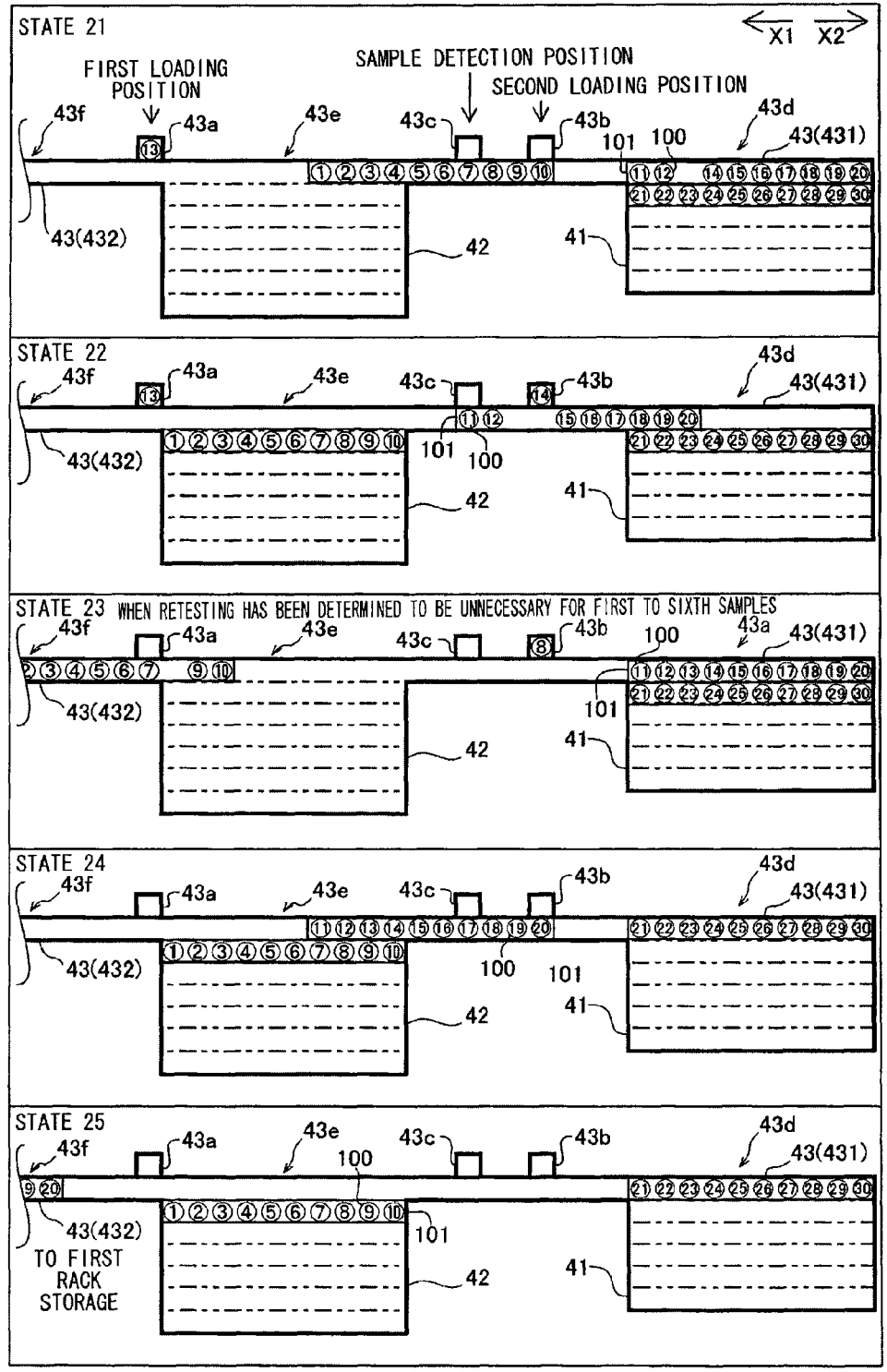
FIG. 20 shows positional relationships between the sample containers accommodated in the racks and each position in the blood analyzer according to the embodiment shown in FIG. 1.
Figure 21:
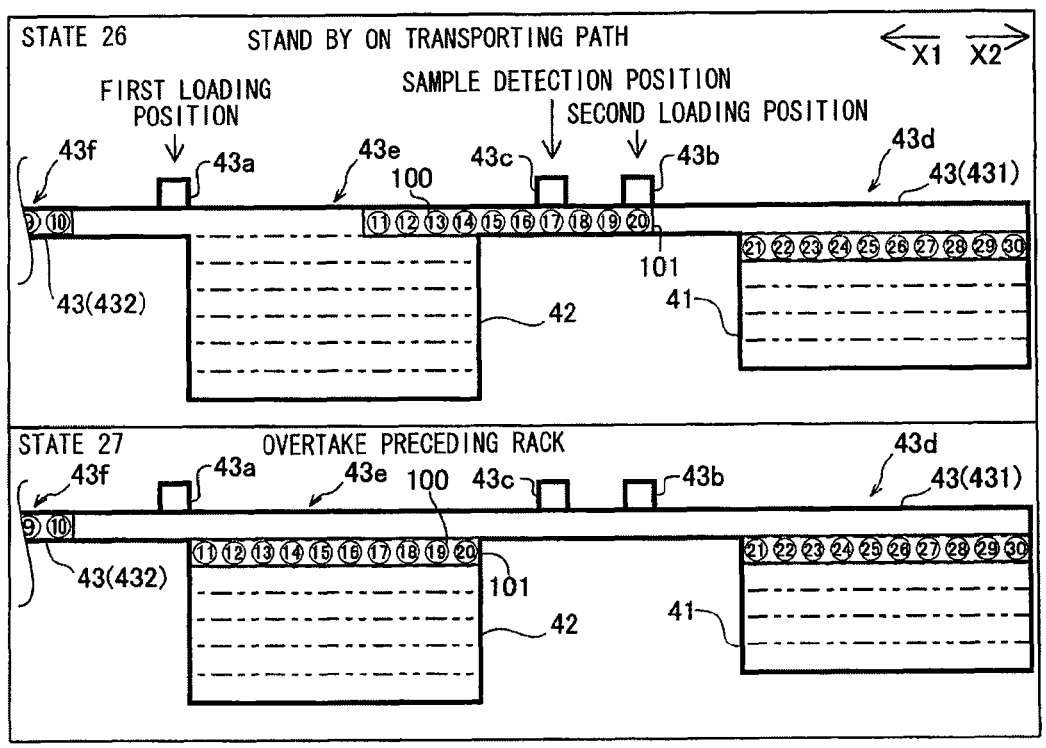
FIG. 21 shows positional relationships between the sample containers accommodated in the racks and each position in the blood analyzer according to the embodiment shown in FIG. 1.

Thereafter, when the preceding rack 101 starts moving toward the second loading position 43b from the standby position 43f of the first rack storage 432, the subsequent rack 101 is again moved to such a position as not to interfere with the movement of the preceding rack 101 (i.e., moved to the vicinity of the feeding position 43d), as shown in STATE 21 of FIG. 20. When the tenth sample container 100 loaded within the second measurement unit 3 is returned to the preceding rack 101, the preceding rack 101 is transferred to the second rack storage 42 as shown in STATE 22. At the time, the subsequent rack 101 is disposed at the second loading position 43b, and the fourteenth sample container 100 is loaded into the second measurement unit 3.

As shown in STATE 22 of FIG. 20, when the preceding rack 101, for which retest determination has been performed for all the samples accommodated therein, is transferred to the second rack storage 42, the subsequent rack 101 becomes the only rack present on the transporting part 431. Therefore, the movements of the subsequent rack 101 thereafter are essentially the same as those of the preceding rack 101.

To be specific, when all of the eleventh to twentieth sample containers 100 (i.e., samples) have been loaded into the measurement units, the processing proceeds to step S48, at which it is determined whether or not the measurement units have loaded sample containers 100 therein. When the measurement units have loaded sample containers 100 therein, positions in the subsequent rack 101, in which the loaded sample containers 100 have previously been accommodated, are located to the loading positions of the measurement units at step S50, whereby the loaded sample containers 100 are returned to the subsequent rack 101. When all the loaded sample containers are returned to the subsequent rack 101 as shown in STATE 24 of FIG. 20, the processing proceeds to step S49.

At step S49, it is determined for all the samples in the subsequent rack 101 whether or not there is a possibility of retesting. When a sample container 100 for which retest determination has not been performed is present in the subsequent rack 101, the processing proceeds to step S52, at which the subsequent rack 101 stays in a standby state in the first rack storage 432 or on the transporting part 431 until retest determination is performed for the sample container 100. Note that when all the eleventh to twentieth sample containers 100 have been returned to the subsequent rack 101, retest determination results are yet to be obtained for, at least, the nineteenth and twentieth samples. Therefore, similarly to the preceding rack 101, the subsequent rack 101 essentially comes into a standby state.

Here, when the preceding rack 101 has already been transferred to the second rack storage 42 as shown in STATE 25 of FIG. 20, the subsequent rack 101 comes into a standby state at the standby position 43f of the first rack storage 432. On the other hand, if the preceding rack 101 is standing by in the first rack storage 432 as shown in STATE 26 of FIG. 21 when the measurement of all the samples (eleventh to twentieth samples) in the subsequent rack 101 has been completed, the subsequent rack 101 stands by on the transporting part 431.

Thereafter, at step S53, it is determined based on retest determination results whether or not a sample to be retested is present in the subsequent rack 101. Here, when a sample to be retested is not present therein, the processing returns to step S49, at which it is determined again for all the samples accommodated in the preceding rack 101 whether or not there is a possibility of retesting. Whereas when a sample to be retested is present therein, interruption retesting is performed in the same manner as that of the preceding rack 101.

When it is determined at step S49 for all the samples in the subsequent rack 101 that there is no possibility of retesting, the processing proceeds to step S51, at which the subsequent rack 101 is transported toward the second rack storage 42. When the subsequent rack 101 is disposed at the transfer position 43e, the subsequent rack 101 is transferred by the rack transfer part 46 to the second rack storage 42. This is the end of all the processes for the subsequent rack 101.

Note that, when the preceding rack 101 is standing by in the standby position 43f of the first rack storage 432 as shown in STATE 26, if it is determined at step S49 for all the samples in the subsequent rack 101 that retesting is unnecessary, then the subsequent rack 101 can be transferred to the second rack storage 42 in advance of the preceding rack 101. In this case, as shown in STATE 27, the subsequent rack 101 is transported to the transfer position 43e from a position, on the transporting part 431, at which the subsequent rack 101 stands by. Then, the subsequent rack 101 is transferred to the second rack storage 42.

In the above manner, the operation of transporting the subsequent rack 101 is performed by the sample transporting apparatus 4.

Figure 22:
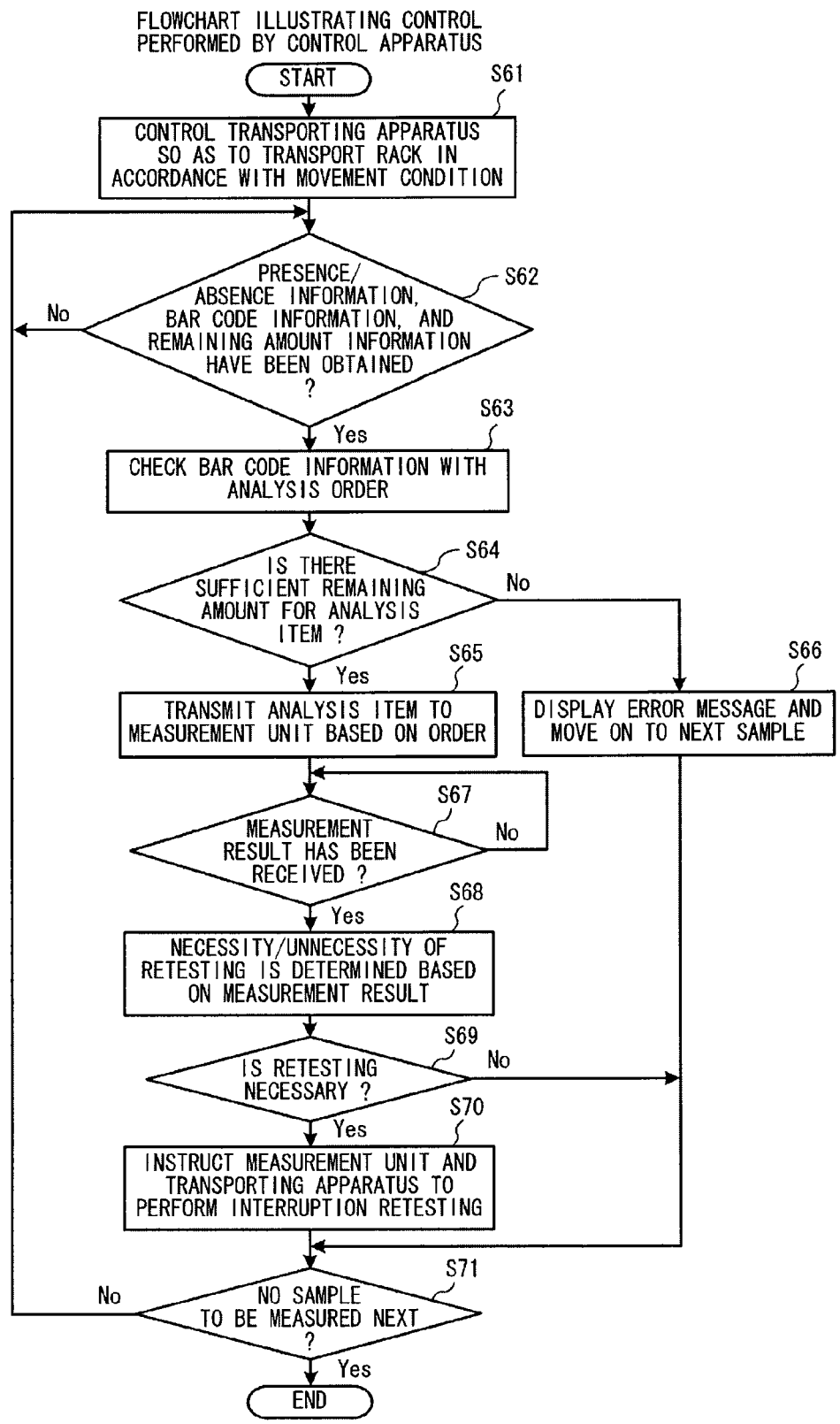
FIG. 22 is a flowchart illustrating the details of control performed by the control apparatus of the blood analyzer according to the embodiment shown in FIG. 1.

FIG. 22 is a flowchart that illustrates control of the measurement units and the sample transporting apparatus by the control apparatus of the blood analyzer according to the embodiment shown in FIG. 1. Described next with reference to FIG. 22 is a process of controlling the measurement units and the sample transporting apparatus 4, which is performed by the control apparatus 5 of the blood analyzer 1 according to the embodiment shown in FIG. 1.

First, as shown in FIG. 22, at step S61, the CPU 51a of the control apparatus 5 performs the above-described operation of transporting the racks 101 in accordance with predetermined movement conditions based on the sampler operation process program 54c stored in the hard disk 51d. To be specific, the protrusions 433d of the first belt 433 are moved to predetermined positions, and these positions are set as original positions of the first belt 433. Then, initialization of the sample transporting apparatus 4 is performed. Thereafter, as shown in STATE 1 to STATE 3 of FIG. 16, a rack 101 is sent out to the transporting part 431 from the rack feeder 41, and transported by the transporting part 431 in the forward direction (X1 direction). Then, each sample container 100 accommodated in the rack 101 is disposed at the sample detection position 43c sequentially. The presence/absence detection sensor 45 detects presence or absence of each sample container 100 accommodated in the rack 101; the bar code reader 44 reads the bar code 100b thereof; and the remaining amount detector 47 detects a remaining amount of the sample therein. Detection results obtained by the presence/absence detection sensor 45 and the remaining amount detector 47, and bar code information read by the bar code reader 44, are transmitted to the CPU 51a of the control apparatus 5 via the communication interface 51g.

At step S62, it is determined whether or not presence/absence information about the samples (sample containers 100) detected by the presence/absence detection sensor 45, bar code information read by the bar code reader 44, and remaining sample amount information detected by the remaining amount detector 47, have been obtained. The operation of transporting the samples toward the sample detection position 43c and the determination at step S62 are repeated until the presence/absence information, the bar code information, and the remaining amount information are obtained. Note that the bar code information and the remaining amount information are obtained only when a presence of a sample container 100 is detected by the presence/absence detection sensor 45.

When the presence/absence information, the bar code information, and the remaining amount information are obtained, the processing proceeds to step S63, at which the CPU 51a checks the bar code information with the analysis orders that specify analysis items for each sample. To be specific, based on the obtained bar code information of a sample container 100, the analysis order of the corresponding sample is obtained from the host computer 6 via the communication interface 51g. From the analysis order, analysis items are obtained for the sample contained in the sample container 100 having the read bar code 100b.

At step S64, based on the obtained analysis items for the sample to be measured and the remaining amount information about the sample which is detected by the remaining amount detector 47, it is determined whether or not the sample in the sample container 100 remains in a sufficient amount that allows measurement to be performed for the analysis items. When it is confirmed based on the remaining amount information that the remaining sample in the sample container 100 is in a sufficient amount, the processing proceeds to step S65. When the remaining sample is not in a sufficient amount for performing the measurement for the analysis items, the processing proceeds to step S66, at which an error message is displayed on the display 52 via the image output interface 51h, indicating that the measurement is not performable due to the insufficient remaining sample amount. Then, the processing proceeds to step S71.

Thereafter, as described above, ten sample containers 100 accommodated in the rack 101 are sequentially transported to the first loading position 43a of the first measurement unit 2 and the second loading position 43b of the second measurement unit 3, so as to be loaded into the measurement units. First, as shown in STATE 4 of FIG. 16, the first sample container 100 is loaded into the first measurement unit 2. Then, the bar code reader 256 reads the bar code 100b of the first sample container 100. The read bar code information is transmitted from the first measurement unit 2 to the CPU 51a of the control apparatus 5 via the communication interface 51g.

Upon receiving the bar code information from the first measurement unit 2, the CPU 51a transmits analysis items for the sample of the first sample container 100 to the first measurement unit 2 via the communication interface 51g at step S65 based on the analysis order corresponding to the received bar code information. As a result, the first measurement unit 2 starts a measurement operation for the sample contained in the first sample container 100.

At step S67, it is determined whether or not measurement results have been received from the first measurement unit 2. When measurement results are not received, the determination step is repeated, waiting for reception of measurement results from the first measurement unit 2. When the first measurement unit 2 has completed the measurement on the sample in the first sample container 100, and measurement results are received accordingly, the processing proceeds to step S68. When the measurement is completed, a position in the rack 101, in which the first sample container has previously been accommodated, is located to the first loading position 43a as shown in STATE 6 of FIG. 17, and the first sample container 100 is returned from the first measurement unit 2 to the rack 101. Although during this period the second measurement unit 3 measures the sample contained in the second sample container 100, a description thereof is omitted here.

At step S68, based on the received measurement results, retest determination is performed for the sample contained in the first sample container 100. To be specific, as shown in step S5 of FIG. 10, based on the measurement results transmitted from the first measurement unit 2, the control section 51 analyzes components that are analysis subjects, and then determines whether or not retesting is necessary. Accordingly, the sample analysis is completed, and the first measurement unit 2 ends the operation for the first sample.

When the retest determination is performed, a determination result indicating whether or not retesting is necessary for the first sample is provided at step S69. When retesting is necessary, the processing proceeds to step S70. On the other hand, when retesting is determined to be unnecessary, all the processes for the first sample end, and the processing proceeds to step S71.

At step S70, the CPU 51a instructs, via the communication interface 51g, the first measurement unit 2 and the sample transporting apparatus 4 to perform interruption retesting. In response to the instruction to perform interruption retesting, presence or absence of the sample to be retested is determined and interruption retesting is performed as shown in steps S18 and S19 of FIG. 11.

Then, presence or absence of a sample to be measured next is determined at step S71. When there is a sample to be measured next, the processing returns to step S62, at which a measurement process is performed for the sample to be measured next. Here, if an instruction to perform interruption retesting has been provided at step S70, the measurement sequence is changed and the sample to be retested is used as a sample to be measured next. Whereas when the measurement and retesting have been completed for all the samples accommodated in the rack 101 and it is determined that there is no sample therein to be measured next, the rack 101 is transported to be transferred to the second rack storage 42 and the processing ends. Note that the above flow describes the measurement process that is performed by the first measurement unit 2 for one sample; however, in reality, similar measurement processes are performed by the first measurement unit 2 and the second measurement unit 3 in parallel.

As described above, the present embodiment includes the transporting part 431 which is configured to be able to transport a rack 101 in the forward direction from the rack feeder 41 to the first rack storage 432, and also in the reverse direction, and able to transport a rack 101 on a path between the rack feeder 41 and the first rack storage 432, the path including the first loading position 43a and the second loading position 43b. The present embodiment also includes the second rack storage 42 for storing a rack 101 which has been transported by the transporting part 431 between the rack feeder 41 and the first rack storage 432 and which accommodates sample containers 100 from which samples have been loaded into the first measurement unit 2 and the second measurement unit 3. Owing to the above configuration, a rack 101 can be temporarily stored in the first rack storage 432 until a determination result is obtained as to whether or not to perform retesting of a sample that has been measured. When it is necessary to perform sample retesting, a rack 101 holding a sample to be retested can be transported in the reverse direction from the first rack storage 432 to the first loading position 43a or to the second loading position 43b. Since this eliminates the necessity to separately provide a returning line dedicated to returning the rack 101 in the reverse direction, the blood analyzer 1 can be reduced in size.

Further, in the present embodiment, the control apparatus 5 is configured to determine, based on test results obtained from the first measurement unit 2 and the second measurement unit 3, whether or not retesting is necessary for the samples in sample containers 100 accommodated in a rack 101. The control apparatus 5 is also configured to control the transporting part 431, based on a result of the necessity/unnecessity determination, so as to transport the rack 101, which stands by in the first rack storage 432, to the first measurement unit 2 or the second measurement unit 3 for retesting, or to the transfer position 43e. Therefore, in accordance with a result of the retest determination for each sample, the rack 101 can be transferred to the second rack storage 42 if there is no necessity of retesting, and the rack 101 can be transported to a measurement unit if retesting is necessary.

Still further, in the present embodiment, the first rack storage 432 is provided in an area that is farther, in the forward direction (X1 direction), than the first loading position 43a, and has the length L that is equivalent to the length of at least one rack 101. Accordingly, loading of sample containers 100 from the subsequent rack 101 can be performed while the preceding rack 101 waiting for retest determination is standing by in the first rack storage 432. Thus, sample processing can be efficiently performed.

Still further, in the present embodiment, the sample transporting apparatus 4 is configured to be able to, when the preceding rack 101 is disposed in the first rack storage 432 and measurement of samples of the subsequent rack 101 that has been sent out onto the transporting part 431 has already started, transport a sample container 100 of the preceding rack 101 (the ninth or tenth sample container 100) to either the first loading position 43a or the second loading position 43b for retesting. Accordingly, even when the measurement of samples of the subsequent rack 101 has already started, the sample container 100 (the ninth or tenth sample container 100) in the preceding rack 101 can be transported, for retesting, to the loading position (the first loading position 43a or the second loading position 43b) of a measurement unit that is ready to perform measurement, immediately after retest determination has been performed for the sample container 100 (the ninth or tenth sample container 100) in the preceding rack 101 that is standing by in the first rack storage 432. Thus, sample processing can be performed with improved efficiency.

Note that the embodiment disclosed herein is merely illustrative in all aspects and should not be recognized as being restrictive. The scope of the present invention is defined by the scope of the claims rather than by the description of the above embodiment, and includes meaning equivalent to the scope of the claims and all modifications within the scope.

For instance, the present embodiment describes the blood analyzer that includes two measurement units that are the first measurement unit and the second measurement unit. However, the present invention is not limited thereto. The blood analyzer may include only one measurement unit, or three or more measurement units.

Further, the present embodiment describes the sample loading with reference to a configuration example in which the sample loading is performed such that, a sample container 100 is removed from a rack 101 by the hand part 251 (351) and the blood contained in the removed sample container 100 is aspirated within the measurement unit by the piercer 211 (311). However, the present invention is not limited thereto. For example, the sample loading may be performed by aspirating a sample from a sample container 100 accommodated in a rack 101 without removing the sample container 100 from the rack 101. In other words, the present invention includes a variation where the sample loading position is the same as the aspirating position.

Still further, the present embodiment describes a configuration example in which the CPU of the control apparatus controls the transporting of racks and the loading of samples, and performs retest determination. However, the present invention is not limited thereto. The rack transporting control, the sample loading control, and the retest determination may be performed by separate control sections, respectively. In this case, the control section for performing the rack transporting control may be provided in the transporting apparatus, and the control section for performing the sample loading control may be provided in each measurement unit. Further, the control section for performing the retest determination may be separately provided.

Still further, the present embodiment describes a configuration example that allows racks 101 to be continuously transported by the first belt 433 and the second belt 434 from the end (the feeding position 43d) of the reverse direction (X2 direction) side of the transporting part 431 to the end (the standby position 43f) of the forward direction (X1 direction) side of the first rack storage 432. However, the present invention is not limited thereto. Racks may be transported by using a different transporting mechanism from the first and second belts. For example, racks may be transported by a transporting mechanism formed with ball screws and ball nuts, or by a transporting mechanism formed with a linear motor.

Still further, the present embodiment describes a configuration example in which a single transporting mechanism (including the first belt 433 and the second belt 434) serves as both the transporting part 431 and the first rack storage 432. However, the present invention is not limited thereto. Separate transporting mechanisms may be formed by using a transporting belt for the transporting part 431 and a transporting belt for the first rack storage 432, respectively, so as to be able to each transport a rack 101.

Still further, the present embodiment describes a configuration example in which the first rack storage 432 has the length L that allows at least one rack 101 (having the width W) to be disposed thereon. However, the present invention is not limited thereto. The first rack storage 432 may have a shorter length than that of a single rack, or may have a greater length than that of two racks.

Still further, the present embodiment describes a configuration example in which the sample transporting apparatus 4 transports multiple racks 101 each holding sample containers 100 containing samples. However, the present invention is not limited thereto. The sample containers may be transported one by one without using a rack.

Still further, the present embodiment gives a description assuming that the retesting of samples that have been measured is performed only once for each sample. However, the present invention is not limited thereto. Retesting may be performed multiple times for each sample.

Still further, the present embodiment describes a configuration example in which when two racks are placed on the transporting part 431 and the first rack storage 432, four samples (the seventh to tenth samples) held by the preceding rack 101 can be measured (and retested) by using both the measurement units, and four samples (the eleventh to fourteenth samples) held by the subsequent rack 101 can be measured (and retested) by using both the measurement units. However, the present invention is not limited thereto. The configuration may be such that three or less samples, or five or more samples, can be measured by using both the measurement units. In this case, the condition for sending out the subsequent rack may be set to be different from obtaining retest determination results for the first to sixth samples of the preceding rack. The condition may be set differently so as to accord with the number of samples that can be measured by using both the measurement units.

Still further, the present embodiment describes movements of the preceding rack 101 and the subsequent rack 101 with reference to the flowcharts in FIGS. 11 to 15. However, the movements described in the present embodiment are merely typical examples for describing the present invention. Accordingly, the transporting operation may be configured to move the preceding rack and the subsequent rack differently from the above-described movements.

Still further, the present embodiment describes an example in which the first loading position 43a is located farther, in the forward direction (X1 direction), than the end of the forward direction side of the second rack storage 42. However, the present invention is not limited thereto. The first loading position may be located farther, in the reverse direction, than the end of the forward direction side of the second rack storage 42.

Still further, the present embodiment describes a configuration example in which the loading of sample containers into the measurement units is performed after presence/absence detection, bar code reading, and remaining amount detection have been performed for all the sample containers accommodated in a rack. However, the present invention is not limited thereto. The loading of sample containers into the measurement units may be performed in parallel with performing the presence/absence detection, bar code reading, and remaining amount detection for the sample containers. To be specific, when presence/absence detection, bar code reading, and remaining amount detection have been performed for the first sample container, the first sample container is loaded into the first measurement unit; thereafter, presence/absence detection, bar code reading, and remaining amount detection are performed for the second sample container, and then the second sample container may be loaded into the second measurement unit.

Still further, the present embodiment describes a configuration example in which the preceding rack is caused to stand by in the first rack storage until retest determination is performed for the samples accommodated therein. However, the present invention is not limited thereto. The preceding rack may be caused to stand by in the first rack storage, depending on the state of the sample transporting apparatus and the measurement units. For example, assume a case where it is necessary to withdraw the preceding rack to a predetermined position, such as a case where synchronization failure has occurred in the sample transporting apparatus with respect to the synchronization between the sample transporting apparatus and the control apparatus and thereby monitoring of the positions of the racks becomes impossible, or a case where a measurement unit has failed in loading a sample container. In these cases, until the state as described above is resolved in the sample transporting apparatus or in the measurement unit, the preceding rack may be caused to stand by in the first rack storage.

Still further, the present embodiment describes a configuration in which the control apparatus 5 determines whether or not retesting is necessary. However, the present invention is not limited thereto. For example, measurement results obtained from the first measurement unit 2 and the second measurement unit 3 may be transmitted to the host computer 6, and the host computer 6 may determine whether or not retesting is necessary. In this case, a result of determination performed by the host computer 6 as to necessity/unnecessity of retesting is transmitted to the control apparatus 5. The control apparatus 5 then performs processing based on the received necessity/unnecessity determination result.

What is claimed is:

1. A sample testing system comprising:
   a test unit for loading and testing a sample in a rack;
   first and second rack storages;
   a rack feeder for feeding a rack to a feed position;
   a transporting part, configured to transport the rack in a first direction and in a second direction that is a reverse direction of the first direction between the first and second rack storages along a single and straight transporting path comprising,
      the feed position where a rack is fed by the rack feeder,
      a standby position corresponding to the first rack storage,
      a transfer position different from the feed position, and
      a sample loading position corresponding to the test unit,
      wherein the first direction is a direction towards the transfer position from the feed position and the sample loading position is located between the standby position and the feed position along the transporting path, wherein the first rack storage extends along the longitudinal axis of the transporting path past the transfer position in the first direction and comprises a length and width that allows the first rack storage to retain a single rack;
   a rack transfer part for transferring the rack present on the transfer position in a perpendicular direction with respect to the second direction to the second rack storage; and
   a controller
   including a memory under control of a processor, the memory storing instructions that, when executed, cause the processor to
      control the transporting part to hold a rack in the standby position until testing result of sample in the rack is obtained;
      control the transporting part to transport the rack in the second direction to return it from the standby position to the sample loading position or to the transfer position, according to the testing result, after obtaining the testing result.

2. The sample testing system of claim 1, the instructions stored in the memory, when executed, further cause the processor to:
   obtain, based on a result of the testing by the test unit, a judgment result of necessity of retesting of the sample in the rack stored in the first rack storage;
   control, based on the judgment result, the transporting part so as to transport the rack to the sample loading position or to the transfer position; and
   control the rack transfer part so as to transfer the rack positioned on the transfer position to the second rack storage.

3. The sample testing system of claim 2, wherein controlling the transporting part comprises
   determining, as a destination of the rack, the transfer position when the judgment result indicates that retesting is unnecessary for the samples of all sample containers accommodated in the rack stored in the first rack storage.

4. The sample testing system of claim 2, wherein controlling the transporting part comprises
   determining, as a destination of the rack, the sample loading position when the judgment result indicates that retesting is necessary for the sample of a sample container accommodated in the rack stored in the first rack storage.

5. The sample testing system of claim 4, wherein controlling the transporting part comprises
   changing the destination of the rack to the transfer position after loading of the sample for the retesting has been performed.

6. The sample testing system of claim 2, wherein the transporting part comprises a transporting belt for transporting the rack in the first direction and the second direction.

7. The sample testing system of claim 6, wherein the transporting part comprises two transporting belts for separately transporting two racks, respectively, the two transporting belts each transporting the corresponding rack in the first direction and the second direction.

8. The sample testing system of claim 7, further comprising a rack feeder for feeding the rack accommodating a sample container to the feed position, wherein the transporting part transports a first rack and a second rack separately, in both the first direction and the second direction, wherein the first rack is fed from the rack feeder and the second rack is fed from the rack feeder so as to follow the first rack.

9. The sample testing system of claim 8, wherein the instructions, when executed, further cause the processor to:
   control the transporting part so as to transport the first rack to the sample loading position;
   control the transporting part so as to transport the first rack to the first rack storage after loading of sample from the first rack has been performed by the test unit; and
   control the transporting part so as to transport the second rack to the sample loading position when the first rack is stored in the first rack storage.

10. The sample testing system of claim 9, wherein the instructions, when executed, further cause the processor to:
    obtain, based on a result of the testing by the test unit, a judgment result of necessity of retesting of a sample in the second rack;
    control the transporting part so as to transport the second rack to the transfer position when the judgment result indicates that retesting is unnecessary for all of the samples in the second rack and the first rack is stored in the first rack storage; and
    control the rack transfer part so as to transfer the second rack to the second rack storage, in advance of the first rack.

11. The sample testing system of claim 2, wherein the instructions, when executed, further cause the processor to:
    control the transporting part such that the samples in the rack are sequentially disposed in the sample loading position in a predetermined sequence;

obtain, based on a result of the testing by the test unit, a result of determination on necessity/unnecessity of retesting of the samples in the rack; and control, when the judgment result indicates that retesting is necessary for a sample, the transporting part so as to dispose the sample at the sample loading position such that the sample interrupts the predetermined sequence.

12. The sample testing system of claim 1, wherein
the test unit comprises a first test unit and a second test unit, and
the transporting part transports the rack such that the samples in the rack are loaded into the first test unit and the second test unit.

13. The sample testing system of claim 1, wherein the transporting part transports the rack in the first direction and the second direction on a transporting path having a width that allows only one rack to at a time pass through.

14. A transporting apparatus for transporting a sample to a test unit that performs loading and testing of a sample in a rack, the transporting apparatus comprising:

first and second rack storages;
a rack feeder for feeding a rack to a feed position;
a transporting part, configured to transport the rack in a first direction and in a second direction that is a reverse direction of the first direction between the first and second rack storages along a single and straight transporting path comprising,
  the feed position where a rack is fed by the rack feeder,
  a standby position corresponding to the first rack storage,
  a transfer position different from the feed position, and
  a sample loading position corresponding to the test unit,
  wherein the first direction is a direction towards the transfer position from the feed position and the sample loading position is located between the standby position and the feed position along the transporting path, wherein the first rack storage extends along the longitudinal axis of the transporting path past the transfer position in the first direction and comprises a length and width that allows the first rack storage to retain a single rack;
a rack transfer part for transferring the rack present on the transfer position in a perpendicular direction with respect to the second direction to the second rack storage; and
a controller comprising a memory under control of a processor, the memory storing instructions that, when executed, cause the processor to
  control the transporting part to hold a rack in the standby position until testing result of sample in the rack is obtained;
  control the transporting part to transport the rack in the second direction to return it from the standby position to the sample loading position or to the transfer position, according to the testing result, after obtaining the testing result.

15. The transporting apparatus of claim 14, wherein the transporting part comprises a transporting belt for transporting the rack in the first direction and the second direction.

16. The transporting apparatus of claim 14, wherein the transporting part comprises two transporting belts for separately transporting two racks, respectively, the two transporting belts each transporting the corresponding rack in the first direction and the second direction.

17. The transporting apparatus of claim 16, wherein the transporting part transports a first rack and a second rack separately, in both the first direction and the second direction, the first rack being fed from the rack feeder and the second rack being fed from the rack feeder so as to follow the first rack.

18. The transporting apparatus of claim 14, wherein the transporting part transports the rack in the first direction and the second direction on a transporting path having a width that allows only one rack at a time to pass through.

* * * * *